United States Patent
Wong et al.

(10) Patent No.: US 12,186,188 B2
(45) Date of Patent: Jan. 7, 2025

(54) SUPPORT DEVICES FOR TRANSCATHETER DELIVERY SYSTEM HANDLES

(71) Applicant: Twelve, Inc., Redwood City, CA (US)

(72) Inventors: Estella Wong, Santa Rosa, CA (US); Joshua Dwork, Santa Rosa, CA (US); Kevin Mauch, Windsor, CA (US); Christopher Switalski, Glastonbury, CT (US); David Grossman, Santa Rosa, CA (US); Mike Simpson, Santa Rosa, CA (US)

(73) Assignee: Twelve, Inc., Redwood City, CA (US)

(*) Notice: Subject to any disclaimer, the term of this patent is extended or adjusted under 35 U.S.C. 154(b) by 911 days.

(21) Appl. No.: 16/862,321

(22) Filed: Apr. 29, 2020

(65) Prior Publication Data

US 2020/0345483 A1 Nov. 5, 2020

Related U.S. Application Data

(60) Provisional application No. 62/841,562, filed on May 1, 2019.

(51) Int. Cl.
*A61F 2/24* (2006.01)
*A61M 25/02* (2006.01)

(52) U.S. Cl.
CPC ............ *A61F 2/243* (2013.01); *A61M 25/02* (2013.01); *A61M 2025/024* (2013.01)

(58) Field of Classification Search
CPC ...... A61F 2/243; A61F 2/2427; A61F 2/9517; A61M 25/02; A61M 2025/024; A61M 25/0113; A61B 2034/301; A61B 34/30
See application file for complete search history.

(56) References Cited

U.S. PATENT DOCUMENTS

| | | | |
|---|---|---|---|
| 2,527,435 A | * | 10/1950 | Little ............... B23K 3/027 248/117.7 |
| 3,924,097 A | * | 12/1975 | Knowles ............ B23K 3/027 219/229 |
| 4,388,735 A | | 6/1983 | Ionescu et al. |
| 4,423,525 A | | 1/1984 | Vallana et al. |
| 4,441,216 A | | 4/1984 | Ionescu et al. |
| 4,629,459 A | | 12/1986 | Ionescu et al. |
| 4,653,577 A | | 3/1987 | Noda |
| 4,666,442 A | | 5/1987 | Arru et al. |

(Continued)

FOREIGN PATENT DOCUMENTS

| | | |
|---|---|---|
| EP | 0224080 B1 | 7/1992 |
| EP | 1088529 B1 | 6/2005 |

(Continued)

OTHER PUBLICATIONS

International Preliminary Report on Patentability, International Appl. No. PCT/US2020/030664, mailed Nov. 2, 2021, 9 pages.

*Primary Examiner* — Amy J. Sterling
(74) *Attorney, Agent, or Firm* — Medler Ferro Woodhouse & Mills PLLC

(57) ABSTRACT

Support devices and associated systems and methods for releasably retaining a delivery system handle while delivering a medical device to a target within a human are described herein. The support device is configured to engage the delivery system handle and enable a user to maneuver a distal end portion of the delivery system by manipulating features of the support device.

22 Claims, 21 Drawing Sheets

(56) References Cited

U.S. PATENT DOCUMENTS

| | | | |
|---|---|---|---|
| 4,671,476 A * | 6/1987 | Yim | B23K 3/027 |
| | | | 248/176.2 |
| 4,679,556 A | 7/1987 | Lubock et al. | |
| 4,686,997 A * | 8/1987 | Oloff | A61B 17/3403 |
| | | | 600/568 |
| 4,758,151 A | 7/1988 | Arru et al. | |
| 4,892,540 A | 1/1990 | Vallana | |
| 5,002,567 A | 3/1991 | Bona et al. | |
| 5,084,151 A | 1/1992 | Vallana et al. | |
| 5,104,406 A | 4/1992 | Curcio et al. | |
| 5,279,578 A * | 1/1994 | Cooke | A61M 5/3213 |
| | | | 604/263 |
| 5,370,684 A | 12/1994 | Vallana et al. | |
| 5,387,247 A | 2/1995 | Vallana et al. | |
| 5,498,242 A * | 3/1996 | Cooke | A61M 5/3213 |
| | | | 128/919 |
| 5,713,953 A | 2/1998 | Vallana et al. | |
| 5,873,812 A | 2/1999 | Ciana et al. | |
| 7,220,277 B2 | 5/2007 | Arru et al. | |
| 7,510,575 B2 | 3/2009 | Spenser et al. | |
| 7,857,845 B2 | 12/2010 | Stacchino et al. | |
| 7,993,392 B2 | 8/2011 | Righini et al. | |
| 8,006,535 B2 | 8/2011 | Righini et al. | |
| 8,034,103 B2 | 10/2011 | Burriesci et al. | |
| 8,057,539 B2 | 11/2011 | Ghione et al. | |
| 8,070,799 B2 | 12/2011 | Righini et al. | |
| 8,109,996 B2 | 2/2012 | Stacchino et al. | |
| 8,114,154 B2 | 2/2012 | Righini et al. | |
| 8,353,953 B2 | 1/2013 | Giannetti et al. | |
| 8,403,982 B2 | 3/2013 | Giannetti et al. | |
| 8,470,024 B2 | 6/2013 | Ghione et al. | |
| 8,486,137 B2 | 6/2013 | Suri et al. | |
| 8,475,521 B2 | 7/2013 | Suri et al. | |
| 8,512,397 B2 | 8/2013 | Rolando et al. | |
| 8,539,662 B2 | 9/2013 | Stacchino et al. | |
| 8,540,768 B2 | 9/2013 | Stacchino et al. | |
| 8,640,521 B2 | 2/2014 | Righini et al. | |
| 8,715,207 B2 | 5/2014 | Righini et al. | |
| 8,808,366 B2 | 8/2014 | Braido et al. | |
| 8,808,367 B2 | 8/2014 | Suri et al. | |
| 8,834,563 B2 | 9/2014 | Righini | |
| 8,840,661 B2 | 9/2014 | Manasse | |
| 8,920,492 B2 | 12/2014 | Stacchino et al. | |
| 9,050,188 B2 | 6/2015 | Schweich, Jr. et al. | |
| 9,056,088 B2 | 6/2015 | Righini et al. | |
| 9,114,010 B2 | 8/2015 | Gaschino et al. | |
| 9,138,314 B2 | 9/2015 | Rolando et al. | |
| 9,149,207 B2 | 10/2015 | Sauter et al. | |
| 9,161,836 B2 | 10/2015 | Rolando et al. | |
| 9,168,105 B2 | 10/2015 | Giannetti et al. | |
| 9,186,249 B2 | 11/2015 | Rolando et al. | |
| 9,204,819 B2 | 12/2015 | Grunwald et al. | |
| 9,248,017 B2 | 2/2016 | Rolando et al. | |
| 9,289,289 B2 | 3/2016 | Rolando et al. | |
| 9,339,207 B2 | 5/2016 | Grunwald et al. | |
| 9,358,105 B2 | 6/2016 | Marchisio et al. | |
| 9,421,094 B2 | 8/2016 | Schweich, Jr. et al. | |
| 9,433,514 B2 | 9/2016 | Quadri | |
| 9,480,559 B2 | 11/2016 | Vidlund et al. | |
| 9,486,313 B2 | 11/2016 | Stacchino et al. | |
| 9,504,835 B2 | 11/2016 | Graindorge | |
| 9,700,413 B2 | 7/2017 | Ruyra Baliarda et al. | |
| 9,750,607 B2 | 9/2017 | Ganesan et al. | |
| 9,788,931 B2 | 10/2017 | Giordano et al. | |
| 9,833,315 B2 | 12/2017 | Vidlund et al. | |
| 9,848,981 B2 | 12/2017 | Suri et al. | |
| 9,867,695 B2 | 1/2018 | Stacchino et al. | |
| 9,895,223 B2 | 2/2018 | Stacchino et al. | |
| 9,895,225 B2 | 2/2018 | Rolando et al. | |
| 9,918,841 B2 | 3/2018 | Righini et al. | |
| 9,974,647 B2 | 5/2018 | Ganesan et al. | |
| 10,058,313 B2 | 8/2018 | Manasse | |
| 10,065,032 B2 | 9/2018 | Ollivier | |
| 10,098,733 B2 | 10/2018 | Righini | |
| 10,117,741 B2 | 11/2018 | Schweich, Jr. et al. | |
| 10,143,550 B2 | 12/2018 | Achiluzzi | |
| 10,213,301 B2 | 2/2019 | Ganesan et al. | |
| 10,245,141 B2 | 4/2019 | Ghione et al. | |
| 10,265,166 B2 | 4/2019 | Schweich, Jr. et al. | |
| 10,285,810 B2 | 5/2019 | Schweich, Jr. et al. | |
| 10,449,039 B2 | 10/2019 | Ganesan et al. | |
| 11,039,903 B2 * | 6/2021 | Marretti | A61B 34/30 |
| 11,259,920 B2 * | 3/2022 | Luong | A61F 2/2427 |
| 11,517,971 B2 * | 12/2022 | Teraoka | B23K 3/027 |
| 2002/0188350 A1 | 12/2002 | Arru et al. | |
| 2008/0045892 A1 | 2/2008 | Ferry et al. | |
| 2008/0147181 A1 | 6/2008 | Ghione et al. | |
| 2008/0262603 A1 | 10/2008 | Giaquinta et al. | |
| 2009/0105794 A1 | 4/2009 | Ziarno et al. | |
| 2010/0076376 A1 | 3/2010 | Manasse et al. | |
| 2012/0158011 A1 | 6/2012 | Sandhu et al. | |
| 2012/0303048 A1 | 11/2012 | Manasse | |
| 2013/0035537 A1 | 2/2013 | Wallace et al. | |
| 2013/0123915 A1 | 5/2013 | Giannetti et al. | |
| 2013/0338766 A1 | 12/2013 | Hastings et al. | |
| 2014/0207011 A1 | 7/2014 | Righini et al. | |
| 2016/0158415 A1 | 6/2016 | Strasly et al. | |
| 2018/0161585 A1 | 6/2018 | Ollivier | |
| 2018/0214263 A1 | 8/2018 | Rolando et al. | |
| 2018/0221147 A1 | 8/2018 | Ganesan et al. | |
| 2018/0235753 A1 | 8/2018 | Ganesan et al. | |
| 2018/0338832 A1 | 11/2018 | Ganesan et al. | |
| 2019/0000618 A1 | 1/2019 | Schweich, Jr. et al. | |
| 2019/0029814 A1 | 1/2019 | Schweich, Jr. et al. | |
| 2019/0142581 A1 | 5/2019 | Maiso et al. | |
| 2019/0183641 A1 | 6/2019 | Ganesan et al. | |
| 2019/0192292 A1 | 6/2019 | Schweich, Jr. et al. | |
| 2021/0228205 A1 * | 7/2021 | Nakadate | A61B 17/0491 |
| 2023/0321405 A1 * | 10/2023 | Scherich | A61M 25/0637 |
| | | | 604/174 |

FOREIGN PATENT DOCUMENTS

| | | |
|---|---|---|
| EP | 1967164 A2 | 9/2008 |
| EP | 2033581 A1 | 3/2009 |
| EP | 2014257 B1 | 9/2010 |
| EP | 2033597 B1 | 3/2011 |
| EP | 2165651 B1 | 8/2011 |
| EP | 1719476 B1 | 11/2011 |
| EP | 2399527 A1 | 12/2011 |
| EP | 2399527 A8 | 3/2012 |
| EP | 2777594 B1 | 9/2014 |
| EP | 2229921 B1 | 11/2014 |
| EP | 2861186 A2 | 4/2015 |
| EP | 2250976 B1 | 8/2015 |
| EP | 3050541 A1 | 8/2016 |
| EP | 3102152 A1 | 12/2016 |
| WO | 2015118464 A1 | 8/2015 |
| WO | 2017062637 A1 | 4/2017 |
| WO | 2017/173331 A1 | 10/2017 |
| WO | 2018/167536 A1 | 9/2018 |
| WO | 2019/069145 A1 | 4/2019 |
| WO | 2019075095 A1 | 4/2019 |
| WO | 2019/209927 A1 | 10/2019 |

* cited by examiner

SUPPORT DEVICES FOR TRANSCATHETER DELIVERY SYSTEM HANDLES

This application claims the benefit of U.S. Provisional Patent Application No. 62/841,562, entitled, "SUPPORT DEVICES FOR TRANSCATHETER DELIVERY SYSTEM HANDLES AND ASSOCIATED SYSTEMS AND METHODS," filed May 1, 2019, the entire content of which is incorporated herein by reference.

TECHNICAL FIELD

The present disclosure relates generally to support devices for transcatheter delivery system handles while delivering a medical device, such as a prosthetic heart valve, to a target site within a human body.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally into the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented in recent years. Examples of pre-assembled, percutaneous prosthetic valves include, e.g., the CoreValve Revalving® System from Medtronic/Corevalve Inc. (Irvine, CA, USA) and the Edwards-Sapien® Valve from Edwards Lifesciences (Irvine, CA, USA). Both valve systems include an expandable frame and a tri-leaflet bioprosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devises may not be well suited for other types of heart valves.

SUMMARY

In some examples, the disclosure describes a support device for releasably retaining a delivery system handle while delivering a medical device to a target site within a human body, the support device comprising: a first base carrying a first support configured to engage a first handle component of the delivery system handle; a second base carrying a second support configured to engage a second handle component of the delivery system handle, wherein at least a portion of the second base is on the first base, wherein the first and second supports extend away from the first and second bases, respectively; and a first translation assembly operably coupled to the first base and the second base, wherein the first translation assembly is configured to slidably translate the second base with respect to the first base, and wherein the first translation assembly is configured to longitudinally translate the second handle component with respect to and independent of the first handle component when the delivery system handle is supported by the support device.

In some examples, the disclosure describes a support device and a catheter system. The support device comprises: a first base carrying a first support configured to engage a first handle component of the delivery system handle; a second base carrying a second support configured to engage a second handle component of the delivery system handle, wherein at least a portion of the second base is on the first base, wherein the first and second supports extend away from the first and second bases, respectively; and a first translation assembly operably coupled to the first base and the second base, wherein the first translation assembly is configured to slidably translate the second base with respect to the first base, and wherein the first translation assembly is configured to longitudinally translate the second handle component with respect to and independent of the first handle component when the delivery system handle is supported by the support device. The catheter system comprises: a first catheter device having a first elongated catheter shaft and a first handle component; and a second catheter device having a second elongated catheter shaft, a second handle component, and a third handle component, the third handle component configured to translate longitudinally with respect to the second handle component, the second elongated catheter shaft having a steerable distal end portion, wherein the second elongated catheter shaft is configured to extend through the first handle component and the first elongated catheter shaft, and wherein the second catheter device is configured to longitudinally translate with respect to the first catheter device.

In some examples, the disclosure describes a method for delivering a device into a heart of a patient, the method comprising: delivering a first distal end portion of a first catheter shaft and a second distal end portion of a second catheter shaft into the heart, wherein the second catheter shaft extends through and is longitudinally slidable with respect to the first catheter shaft; supporting a first handle component on a first base assembly, wherein the first handle component is coupled to a first proximal portion of the first catheter shaft; supporting a second handle component on a second base assembly, wherein the second handle component is coupled to a second proximal portion of the second catheter shaft; supporting a third handle component on a third base assembly; translating the second base assembly with respect to the first base assembly to longitudinally translate the second handle component with respect to the first handle component, wherein the longitudinal translation of the second handle component translates the second distal end portion of the second catheter shaft along a first plane; and translating the third base assembly with respect to the second base assembly to longitudinally translate the third handle component with respect to the first handle component and the second handle component, wherein the longitudinal translation of the third handle component translates a distal end portion of a third catheter shaft relative to the to the second distal end portion.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

DETAILED DESCRIPTION

Figure 1:
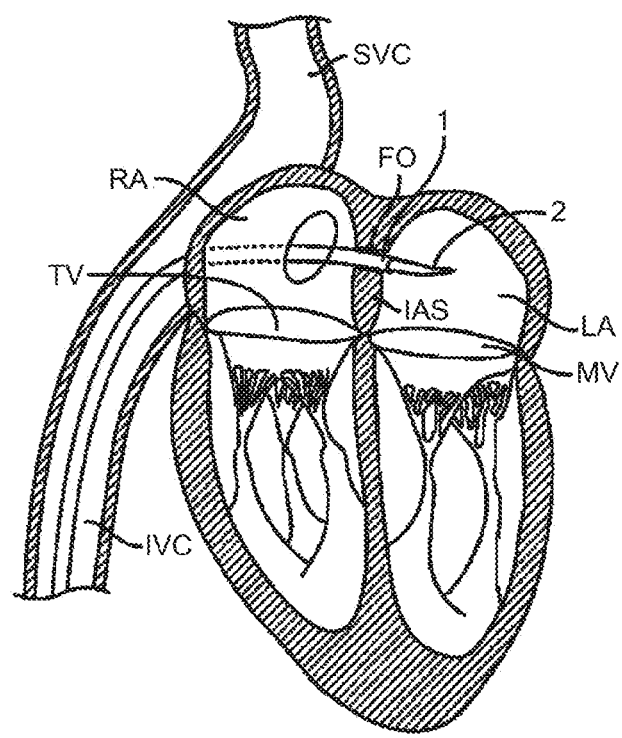
FIG. 1 is a schematic, cross-sectional illustration of the heart showing an antegrade approach to the native mitral valve from the venous vasculature in accordance with various examples of the present disclosure.

The present disclosure is generally directed to support devices for transcatheter delivery system handles and associated systems and methods. Specific details of several examples of the present disclosure are described herein with reference to FIGS. 1-16. Although many of the examples are described with respect to handle assemblies, devices, systems, and methods for delivering prosthetic heart valve devices to a native mitral valve, other applications and other examples in addition to those described herein are within the scope of the present disclosure. For example, at least some examples of the present disclosure may be useful for delivering prosthetic valves to other native valves, such as the tricuspid valve or the aortic valve. In addition, examples of the present disclosure may also be used to deliver other medical devices to the heart (e.g., heart valve repair devices, annuloplasty devices) and/or intravascularly deliver medical devices to other sites within the body. It should be noted that other examples in addition to those disclosed herein are within the scope of the present disclosure. Moreover, a person of ordinary skill in the art will understand that examples of the present disclosure can have configurations, components, and/or procedures in addition to those shown or described herein and that these and other examples can be without several of the configurations, components, and/or procedures shown or described herein without deviating from the present disclosure.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Several examples of the present disclosure are directed to support devices for releasably retaining delivery system handles while delivering a medical device to a target site within a human body. The support devices disclosed herein address the unique challenges of transcatheter replacement or repair of native heart valves, such as intravascular implantation of prosthetic mitral heart valve devices. Compared to replacing aortic valves, mitral valve replacement faces unique anatomical obstacles that can render mitral valve replacement significantly more challenging than aortic valve replacement. For example, the chordae tendineae of the left ventricle may present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning and anchoring a valve replacement device on the ventricular side of the native mitral valve annulus is complicated. In addition, navigating a catheter via a transfemoral, transseptal, or transapical approach to the mitral valve and into position with respect to the native annulus can also prove difficult given the complexities of the vascular and cardiac anatomies. Thus, during transcatheter mitral valve replacement, the support systems disclosed herein facilitate efficient and precise deployment to reduce procedure times and promote accurate positioning of the prosthetic heart valve relative to the native annulus, leaflets, left atrium, and left ventricular outflow tract.

Examples of the present disclosure also provide systems, methods and devices to deliver prosthetic heart valves to the body, such as the mitral valve, that address the challenges associated with the anatomy along the intravascular path to the mitral or tricuspid valve. The systems and methods enable a percutaneous approach using a catheter delivered intravascularly through a vein or artery into the heart, or through a cannula inserted through the heart wall. For example, the apparatus and methods are particularly well-suited for trans-septal and trans-apical approaches, but can also be trans-atrial and direct aortic delivery of a prosthetic replacement valve to a target location in the heart. Additionally, the examples of the devices and methods as described herein can be combined with many known surgeries and procedures, such as known methods of accessing the valves of the heart (e.g., the mitral valve or tricuspid valve) with antegrade or retrograde approaches, and combinations thereof.

The systems and methods described herein facilitate controlled delivery of a prosthetic heart valve device using trans-apical or trans-septal delivery and allow for fine adjustments of the prosthetic heart valve device during deployment. Specifically, the support devices described herein can releasably retain a delivery system handle during at least a portion of an implantation procedure. The support devices include features that allow a clinician to precisely manipulate portions of a delivery handle to maneuver a distal end of a delivery catheter coupled to the delivery handle. Further, by fully supporting the delivery system handle, the clinician does not need to hold the handle and, therefore, the support device enables the clinician to use both hands to fine-tune the position of the distal end of the delivery catheter. Accordingly, the support device provides for precise device deployment at the target site.

To better understand the structure and operation of valve replacement devices in accordance with the present disclosure, it is helpful to first understand approaches for implanting the devices. The mitral valve or other type of atrioventricular valve can be accessed through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well known and described in the patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
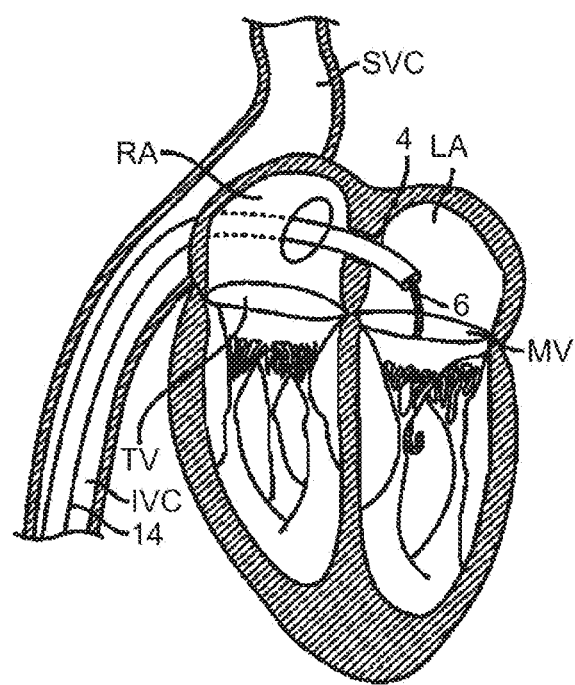
FIG. 2 is a schematic, cross-sectional illustration of the heart showing access through the inter-atrial septum (IAS) maintained by the placement of a guide catheter over a guidewire in accordance with various examples of the present disclosure.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the disclosure.

In an alternative antegrade approach (not shown), surgical access may be obtained through an intercostal incision, such as without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches may enable more precise and effective centering and stabilization of the guide catheter and/or prosthetic valve device. The antegrade approach may also reduce the risk of damaging the chordae tendinae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
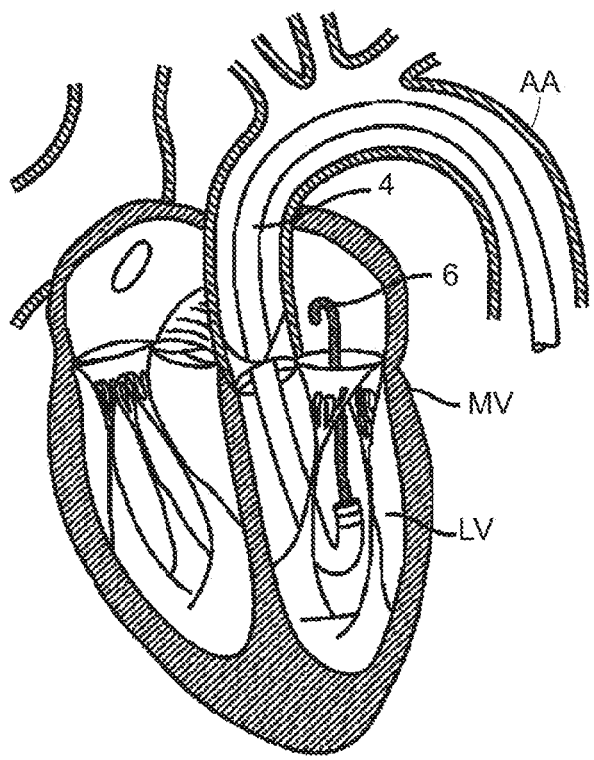
FIGS. 3 and 4 are schematic, cross-sectional illustrations of the heart showing retrograde approaches to the native mitral valve through the aortic valve and arterial vasculature in accordance with various examples of the present disclosure.
Figure 4:
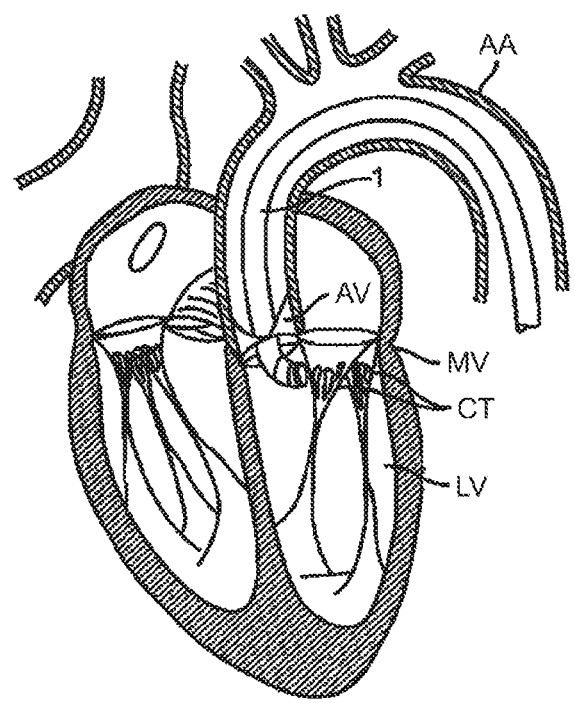

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, such as intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Some cardiologists also more commonly use retrograde approaches, and thus retrograde approaches may be more familiar to some cardiologists.

Figure 5:
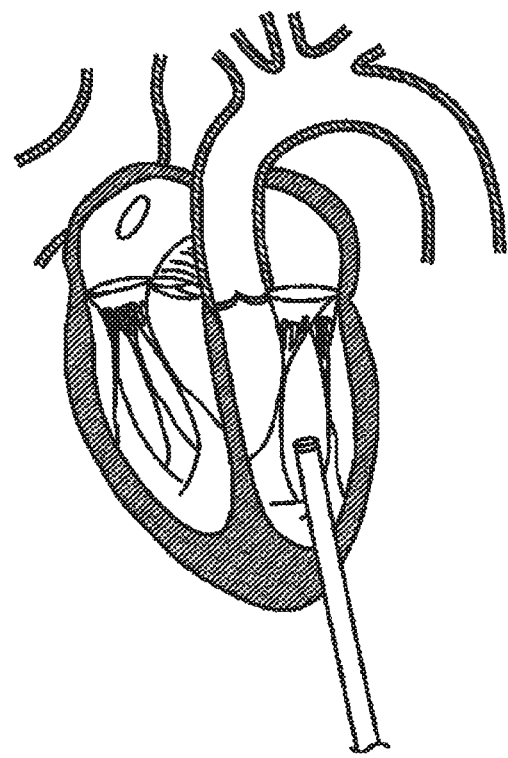
FIG. 5 is a schematic, cross-sectional illustration of the heart showing an approach to the native mitral valve using a trans-apical puncture in accordance with various examples of the present disclosure.

FIG. 5 shows a trans-apical approach via a trans-apical puncture. In this approach, access to the heart is via a thoracic incision, which can be a conventional open thoracotomy or sternotomy, or a smaller intercostal or subxyphoid incision or puncture. An access cannula is then placed through a puncture in the wall of the left ventricle at or near the apex of the heart. The catheters and prosthetic devices described herein may then be introduced into the left ventricle through this access cannula. The trans-apical approach provides a shorter, straighter, and more direct path to the mitral or aortic valve. Further, because it does not involve intravascular access, the trans-apical approach does not require training in interventional cardiology to perform the catheterizations required in other percutaneous approaches.

Figure 6A:
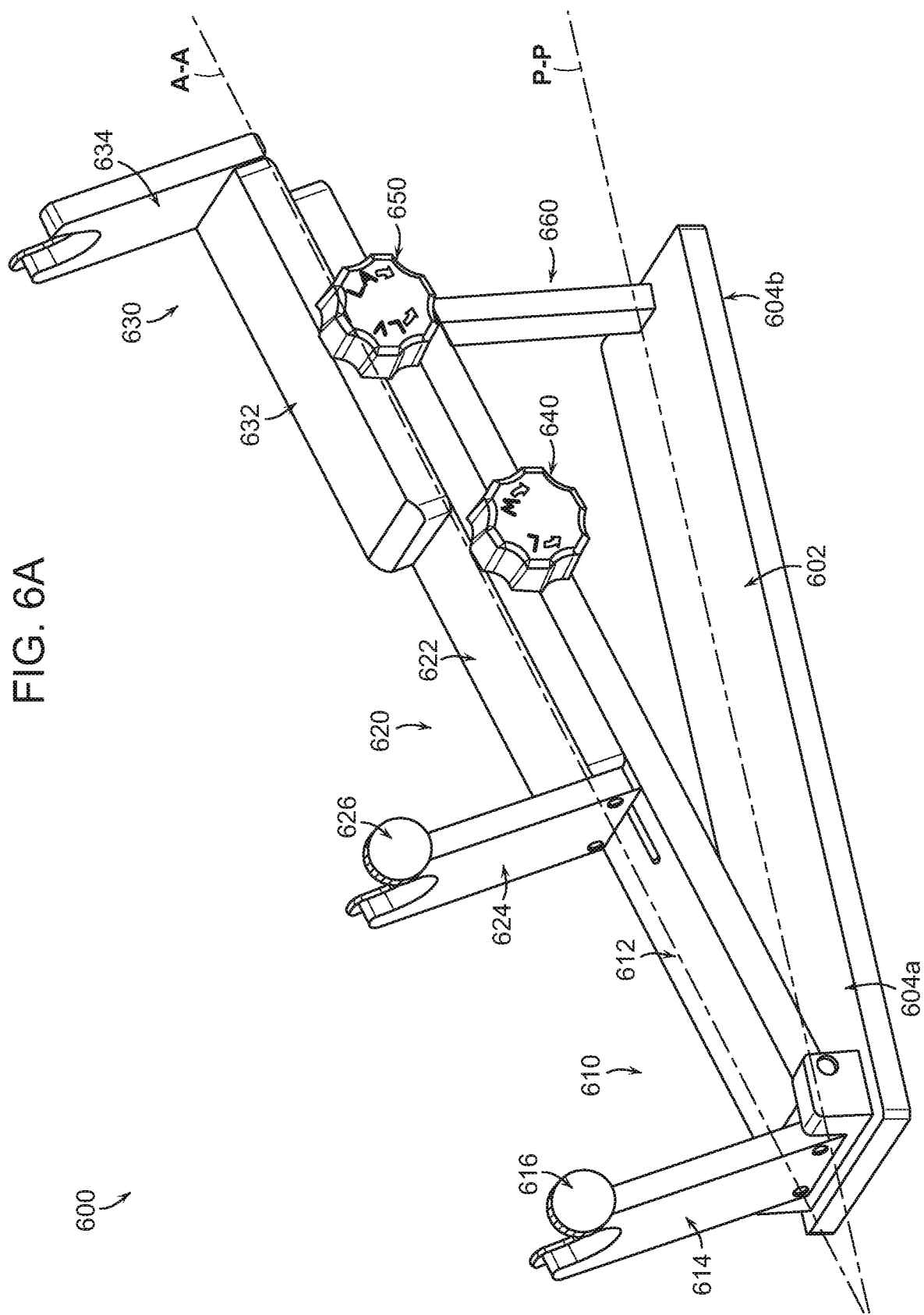
FIG. 6A is an isometric view of a support device configured in accordance with examples of the present disclosure.
Figure 6B:
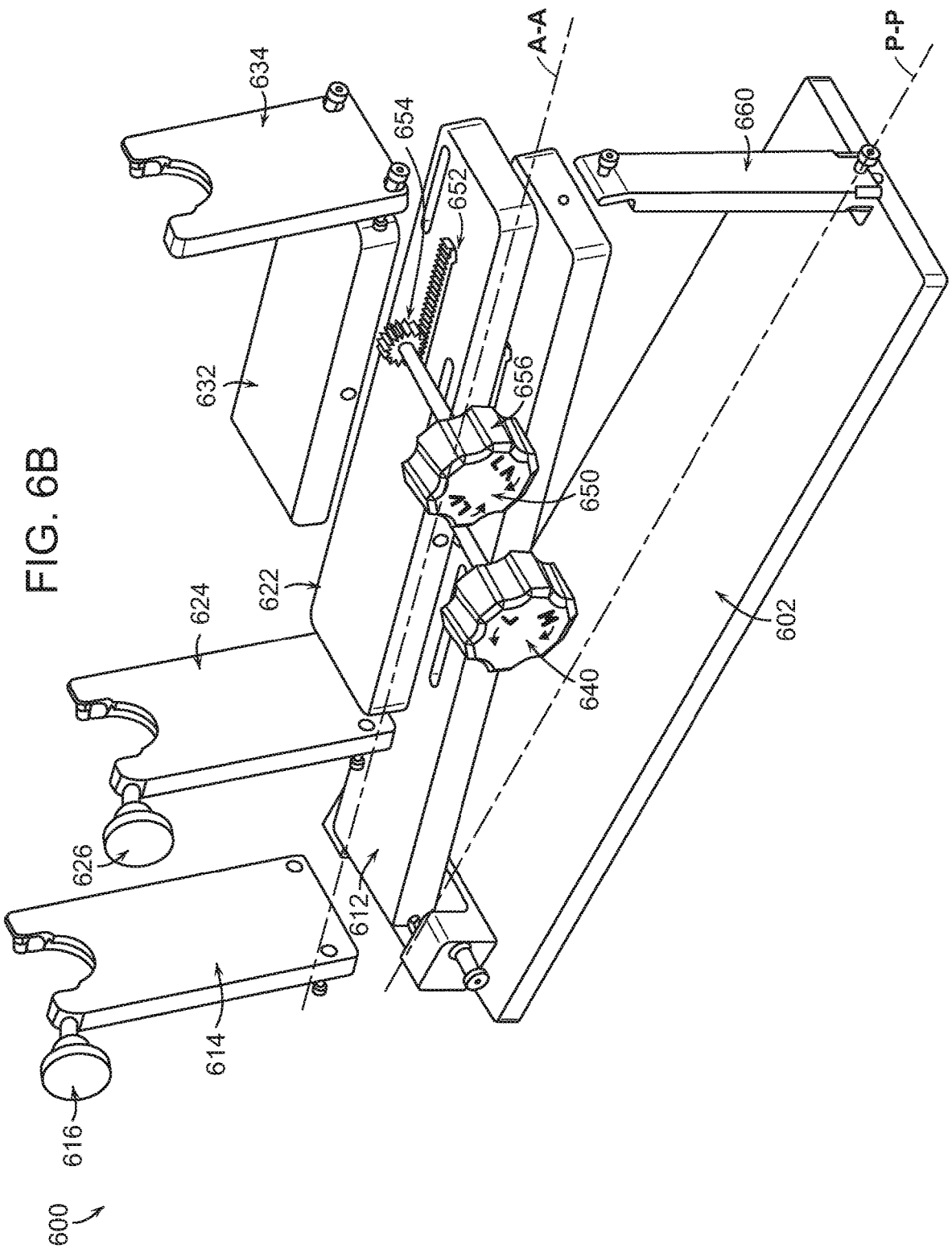
FIG. 6B is an exploded isometric view of the support device of FIG. 6A.

FIG. 6A is an isometric view of a support device 600 configured in accordance with some examples of the present disclosure, and FIG. 6B is an exploded isometric view of the support device 600. The support device 600 includes a platform 602 that carries one or more base assemblies (referred to individually as a first base assembly 610, a second base assembly 620, and a third base assembly 630; referred to collectively as "base assemblies 610, 620, 630"), and the base assemblies 610, 620, 630 may include components used to retain various portions of a delivery system (not shown) that remain outside of a patient's body during a delivery procedure, such as a delivery system handle and/or a proximal portion of a catheter. In the example illustrated in FIGS. 6A and 6B, for example, the first base assembly 610 can be configured to engage a first handle component of the delivery system handle, the second base assembly 620 can be configured to engage a second handle component of the delivery system handle, and the third base assembly 630 can be configured to engage a third handle component of the delivery system handle. The support device 600 is shown engaged with delivery system handles in FIG. 6C.

The support device 600 further includes one or more translation assemblies (identified individually as a first translation assembly 640 and a second translation assembly 650; referred to collectively as "translation assemblies 640, 650") operably coupled to two of the base assemblies 610, 620, 630 to provide for linear translation of the base assemblies 610, 620, 630 with respect to each other. In the illustrated example, the first translation assembly 640 is operably coupled to the first and second base assemblies 610 and 620 and configured to slidably translate the second base assembly 620 with respect to the first base assembly 610. The second translation assembly 650 is operably coupled to the second and third base assemblies 620 and 630 and configured to slidably translate the third base assembly 630 with respect to the second base assembly 620. During a delivery procedure, the delivery system handle(s) is releasably retained by the support device 600, and the first translation assembly 640 provides for longitudinal translation of the second handle component with respect to and independent of the first handle component, while the second translation assembly 650 provides for longitudinal translation of the third handle component with respect to and independent of the second handle component.

The platform 602 has a first end portion 604a and a second end portion 604b (collectively referred to as "end portions 604") and can define a platform axis P-P that extends through the end portions 604. The first end portion 604a of the platform 602 can correspond to a distal end portion of the platform (i.e., closer to the distal end portion of the delivery system catheter) and the second end portion 604b can correspond to a proximal end portion of the platform 602 (i.e., further from the distal end portion of the delivery system catheter). The platform 602 can include a surface that provides a stable base structure for other components of the support device 600, such as the base assemblies 610, 620, 630. A footprint of the platform 602 may be generally rectangular (depicted in FIG. 6A), square, oval, or any other suitable shape for stabilizing the components carried thereon. In some examples, the platform 602 may include features that are configured to temporarily or permanently affix the support device 600 to an underlying or adjacent structure such that the platform 602 remains at least substantially stationary during a delivery procedure. For example, the underlying surface of the platform 602 may have a texture and/or an adhesive, and/the support device 600 may include a fastener (e.g., a clamp) that is configured to secure the platform 602 to another structure (e.g., a procedure table, a surgical tool table).

As shown in FIG. 6A, the first base assembly 610 may include a first base portion 612 and a first support 614 configured to engage the first delivery handle component, the second base assembly 620 may include a second base portion 622 and a second support 624 configured to engage the second delivery handle component, and the third base assembly 630 may include a third base portion 632 and a third support 634 configured to engage the third delivery handle component. The supports 614, 624, 634 can extend generally away from the platform 602 and, as shown in FIG. 6A, may be generally perpendicular to the corresponding base portions 612, 622, 632. The base assemblies 610, 620, 630 can be positioned successively along the platform axis P-P and each base portion 612, 622, 632 may partially overlap the adjacent base portion(s) 612, 622, 632. In the illustrated example, for example, the first base assembly 610 is positioned proximate to the first end portion 604 of the platform 602, and the first base portion 612 is positioned between the platform 602 and the second base portion 622 of the second base assembly 620. The second base assembly 620 is positioned so that the second base portion 622 is positioned between the first base portion 612 and the third base portion 632.

In some examples, the base portion 612, 622, 632 and their respective supports 614, 624, 634 may be two separate components secured together by one or more fasteners and/or adhesives, such as screws and/or glue. In other examples, the base portions 612, 622, 632 may be integrally manufactured with their respective supports 614, 624, 634 such that they together form a unitary structure. The base portions 612, 622, 632 may be generally rectangular and have a first terminus proximate to the first end portion 604 of the platform 602 and a second terminus spaced apart from the first end portion 604 of the platform 602 along the platform axis. An axis A-A extends through the first and second termini of the base portions 612, 622, 632.

A first end region of the supports 614, 624, 634 may be connected or otherwise coupled to their respective base portions 612, 622, 632 at any point at or between the first and second termini. A second end region of each support 614, 624, 634 include features that are configured to engage a portion of the delivery system handle. The second end regions of the supports 614, 624, 634 may releasably secure the delivery system handle to the base assemblies 610, 620, 630 via fasteners or physical mating surfaces. For example, the first support may include a first fastener 616, and the second support may include a second fastener 626. The first and/or second fasteners 616, 626 may include a knob operably coupled to a screw (e.g., a locking thumb screw) configured to prevent linear and/or rotational translation of the handle with respect to the platform 602. In some examples, the third support 634 may include a back-cradle support extending from the third support 634 and configured to engage an end portion of the handle and/or mate with a corresponding surface of the handle. In addition to or in place of the fasteners, the delivery system handle may have one or more flanges (not shown) that may couple to support grooves in the second end portion of one or more of the supports 614, 624, 634 and thereby prevent linear and/or rotational translation of the handle with respect to the supports. Other suitable arrangements of fasteners beyond those depicted are included in the present disclosure. For example, in some examples, the first, second, and third supports 614, 624, 634 may include a first, second, and third fastener, and in other examples only one of the supports 614, 624, 634 includes a fastener. One skilled in the art will recognize that a variety of base assemblies may be configured as disclosed herein and are thus within the scope of the present disclosure.

The base assemblies 610, 620, 630 are operably coupled to each other via the first translation assembly 640 and the second translation assembly 650. The translation assemblies 640, 650 may take any form capable of sliding or otherwise linearly translating the base assemblies 610, 620, 630 with respect to each other. For example, as further illustrated with respect to FIG. 6B, the second translation assembly 650 can include a rack 652 (e.g., a track with teeth or other mating surfaces), a pinion 654 (e.g., a gear that includes surfaces, such as teeth, that mesh with the surfaces of the rack 652), and a knob 656 or other actuator. The pinion 654 is operably coupled to both the rack 652 and the knob 656 such that manipulating (e.g., rotating) the knob 656 causes the pinion 654 to rotate. This rotation causes the pinion 654 to mesh with successive teeth of the rack 652 to longitudinally translate the pinion 654 and the rack 652 with respect to each other. Because the rack 652 is attached to the second base assembly 620 and the pinion is attached to the third base assembly 630, this longitudinal translation causes the second base 622 and the third base 632 to move linearly relative to each other. The first translation assembly 640 may also include a rack, a pinion, and a knob (i.e., a first rack, a first pinion, and a first knob), which operate in a substantially similar manner as the second translation assembly 650 as described herein, although the rack may be attached to the first base assembly 610, and the longitudinal translation of the pinion and rack causes the first base 612 and second base 622 to move linearly with respect to each other.

In some examples, the support device 600 may also include one or more spacing component(s) 660 that separate one or more of the base assemblies 610, 620, 630 from the platform 602. For example, the spacing component 660 can space the third base assembly 630 apart from the second end portion 604b of the platform 602 such that the base assemblies 610, 620, 630 define an acute angle relative to the platform 602. The spacer component 660 may be a shaft or other type of longitudinal support that extends perpendicular or at an angle relative to the platform axis P-P and allows one or more of the bases 612, 614, 616 to be supported thereby. As such, the spacer component 660 can space apart the second end portion 604b of the platform 602 from at least a portion of the third base 632. In other examples, the spacer component 660 may take another form suitable to space apart the platform 602 and at least a portion of the third base 632, such as a ratchet wheel. This defines an acute angle between the platform axis P-P and the longitudinal axis A-A of the first, second, and/or third base assembly 610, 620, 630. In some examples, the angle defined by the platform axis and the first axis may be between 10 degrees and 40 degrees, between 15 degrees and 35 degrees, or between 20 degrees and 30 degrees. For example, the angle may be about 10 degrees, about 15 degrees, about 20 degrees, about 25 degrees, about 30 degrees, about 35 degrees, or about 40 degrees. In addition, the spacer component 660 may be either fixed or adjustable. If the spacer component 660 is adjustable, then the acute angle formed between the platform axis P-P and the longitudinal axis A-A may be increased or decreased by adjusting the height of the spacer component 660. In operation, when the delivery system handle is carried by the support device 600, the spacer component 660 positions the delivery system handle at an appropriate angle of approach for the delivery system catheter into the patient's body to facilitate device delivery. This angle may differ based on the target site of the device, the point of entry into the patient, and/or the patient's specific anatomy.

Figure 6C:
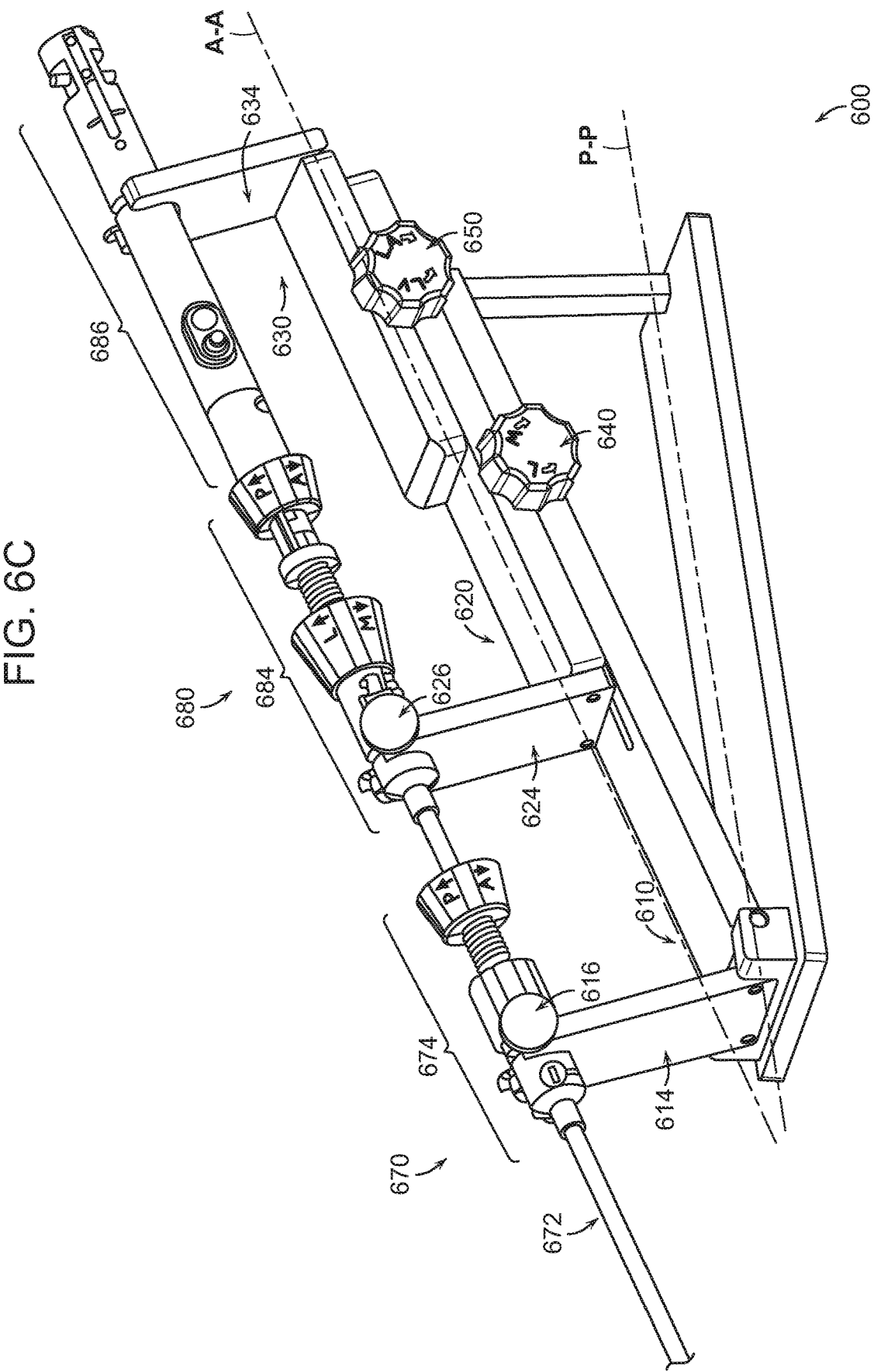
FIG. 6C is an isometric view of the support device of FIG. 6A releasably retaining a delivery system handle in accordance with some examples of the present disclosure.

FIG. 6C is an isometric view of the support device 600 of FIG. 6A with delivery system handles releasably retained in its supports 614, 624, 634 in accordance with some examples of the present disclosure. In the illustrated example, the delivery system includes a first catheter device 670 having a first elongated catheter shaft 672 and a first handle component 674, a second catheter device 680 having a second elongated catheter shaft (not shown) extending through the first elongated catheter shaft 672 and a second handle component 684, and a third handle component 686 having a third elongated catheter shaft (not shown) extending through the second elongated catheter shaft. The first elongated catheter shaft 672 of the first catheter device 670 and/or the second elongated catheter shaft of the second elongated catheter device 680 may include a steerable distal end portion (shown in FIG. 6D and discussed below). The first support 614 of the first base assembly 610 releasably retains the first handle component 674, the second support 624 of the second base assembly 620 releasably retains the second handle component 684, and the third support 634 of the third base assembly 630 releasably retains the third handle component 686. As described above with respect to FIG. 6A, the first handle component 674 and the second handle component 684 may be secured to the support device 600 by a first fastener 616 and a second fastener 626, respectively. Additionally, or alternatively, the first and/or second handle components 674 and 684 may have flanges configured to mate with grooves on the first and/or second supports 614 and 624 to prevent linear and/or rotation translation of the handle when retained by the support device 600. The third handle component 686 may be secured in place by a back-cradle support extending from the third support 634 of the third base assembly 630.

The support device 600 may be configured to impart movement at the steerable distal end portion of the second elongated catheter and the distal end portion of the third elongated catheter shaft when the delivery system handle is retained in the device 600. For example, when the first translation assembly 640 slidably translates the second base assembly 620 with respect to the first base assembly 610, the second handle component 680 (and the third handle component 686) longitudinally translates with respect to the first handle component 670. This causes the steerable distal end portion of the second elongated catheter shaft to move along a first plane relative to the first elongated catheter shaft 672 (e.g., in a proximal-distal direction). When the second translation assembly 650 slidably translates the third base assembly 630 with respect to the second base assembly 620, the third handle component 686 longitudinally translates with respect to the second handle component 684. Depending upon the relative configuration of the steerable catheters, this can cause a distal end portion of a third elongated catheter shaft (which is connected to the third handle component 686) to move along a second plane or the first plane (e.g., to advance into the left ventricle LV or retract into the left atrium LA relative to the second catheter device 680). Additionally, in some examples, the distal end portion of the second elongated catheter shaft may be steered by turning the knob labeled with L and M adjacent to the second support 624, and the second and third elongated catheter shafts may be rotated using the knob labeled P and A on third handle component 686.

Figure 6D:
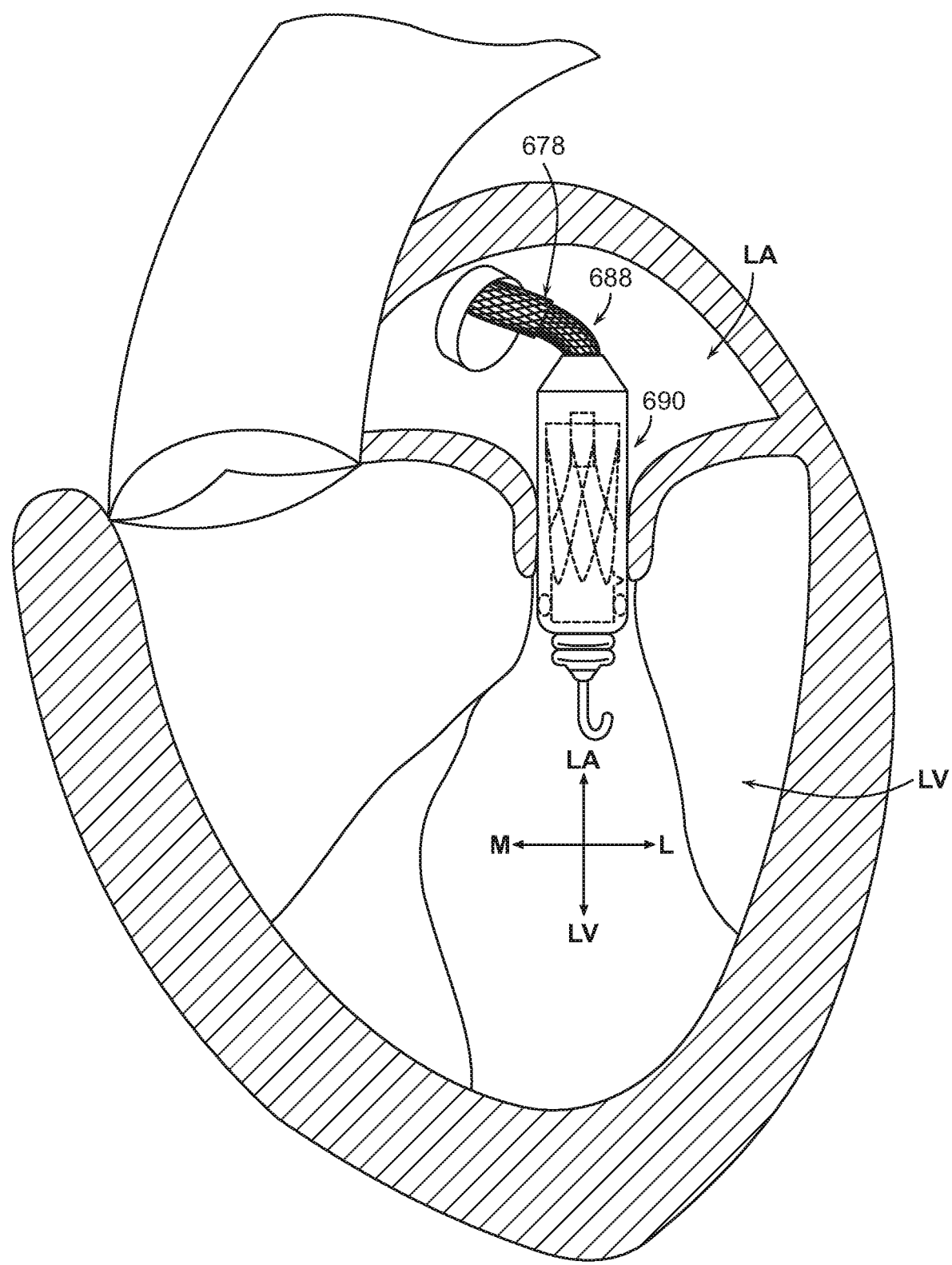
FIG. 6D is an of a distal end portion of an example dual shaft delivery catheter during deployment of a prosthetic mitral valve device within a human heart in accordance with some examples of the present disclosure.

FIG. 6D illustrates a distal end portion 678 of the first catheter device 670 and a distal end portion 688 of the second catheter device 680 of FIG. 6C deployed near the mitral valve of a human heart. A delivery capsule 690 may be carried by the distal end portion of the elongated catheter shaft of the third catheter device 686 and is positioned adjacent the mitral valve annulus. In such examples, the first translation assembly 640 is configured to translate the steerable distal end portion 688 of the second elongated catheter shaft, together with the distal end portion of the third elongated catheter shaft proximally and distally relative to the distal end portion 678 of the first catheter device 670. The direction (e.g., LA-LV or M-L) along which this translation occurs may be controlled based on the orientation of the steerable distal end portion 688, which may be controlled by turning the knob labeled with L and M that is part of the second handle component 684. For example, turning the knob labeled with L and M in a first direction causes the steerable distal end portion 688 to orient in a lateral L direction, and turning the knob labeled with L and M in a second direction may cause the steerable distal end portion 688 to orient in a medial M direction. The second translation assembly 650 is configured to translate the distal end portion of the third elongated catheter shaft relative to the steerable distal end portion 688 of the second elongated catheter shaft, which may cause the capsule 690 to advance or retract relative to the left atrium LA and the left ventricle LV of the human heart. For example, turning the second knob of the second translation assembly 650 in a first direction may cause the distal end portion of the third elongated catheter shaft and the capsule 690 to extend towards the left ventricle LV, and turning the second knob in a second direction may cause the distal end portion of the third elongated catheter shaft and the capsule 690 to retract towards the right atrium RA. Thus, a clinician may use the first and second knobs of the first and second translation assemblies 640 and 650, alone with the knob labelled with L and M that is part of the second handle component 684 to adjust the steerable distal end portion 688 of the second catheter shaft and the third catheter shaft coupled to the third catheter device 686 which includes a delivery capsule 690 to ensure the delivery capsule 690 is correctly positioned to deploy a prosthetic device.

FIGS. 7-14 are isometric views of support devices 700, 800, 900, 1000, 1100, 1200, 1300, and 1400, respectively, configured in accordance with some examples of the present disclosure. The support devices 700, 800, 900, 100, 1100, 1200, 1300, and 1400 can include various features generally similar to the features of the support device 600 described above with respect to FIGS. 6A-6D, even if not explicitly discussed with respect to these examples. One of ordinary skill in the art will recognize that the features discussed above can be utilized with the examples discussed below.

Figure 7:
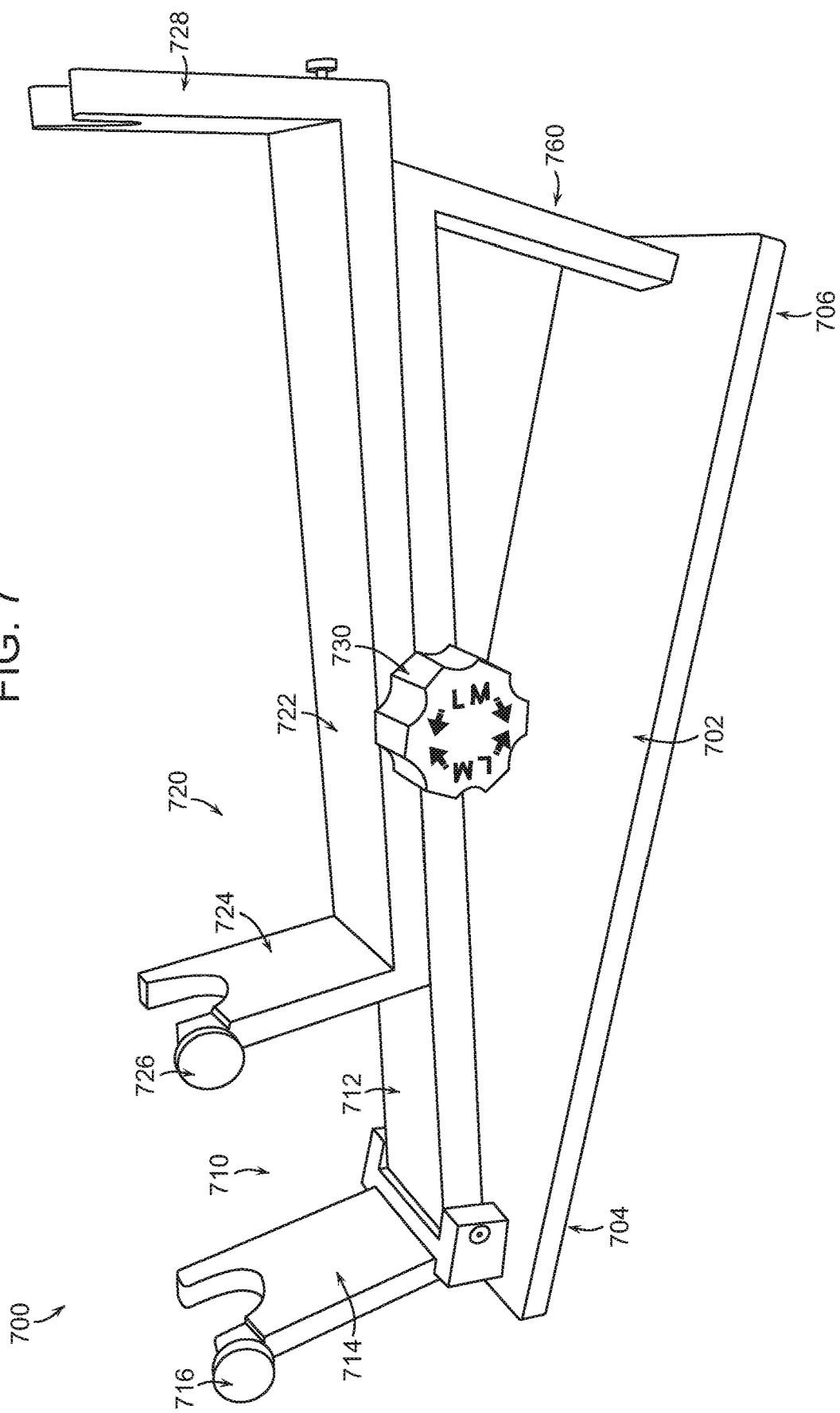
FIG. 7 is an isometric view of a support device configured in accordance with some examples of the present disclosure.

Referring to FIG. 7, the support device 700 has a platform 702 with a first end portion 704 and a second end portion 706, and a first base assembly 710 having a first base portion 712 and a first support 714 configured to engage a first handle component of a delivery system handle. The support device further includes a second base assembly 720 having a second base portion 722 and a second support 724 configured to engage a second handle component of the delivery system handle, and a third support 728 configured to engage a third handle component of the delivery system handle. The first, second, and third supports 714, 724, 728 extend in a direction away from the platform 702. The first and second supports 714 and 724 include fasteners 716 and 726, respectively, and are configured to secure the delivery system handle to the support device 700. The support device 700 further includes a translation assembly 730 operably coupled to the first and second base assemblies 710 and 720. The translation assembly 730 is configured to slidably translate the second base assembly 720 with respect to the first base assembly 710. To facilitate this, in some examples, the translation assembly 730 may include a rack, a pinion, and a knob (as described above with respect to FIG. 6B). The pinion may be operably coupled to both the rack and the knob, such that manipulating the knob causes the pinion to rotate and thus causes the rack to longitudinally translate with respect to the pinion. The rack may be attached to the first base assembly 710 such that this longitudinal translation causes the first base portion 712 and the second base portion 722 to move relative to each other. The support device 700 may also include a spacing component 760 that separates the second end portion 706 of the platform 702 from at least a portion of the second base assembly 720.

The support device 700 may releasably retain a delivery system handle having at least a first handle component and a second handle component. When the support device retains the delivery system handle, the translation assembly 730 is configured to longitudinally translate the second handle component with respect to and independent of the first handle component. To do so, the knob may be manipulated by a user, thereby causing the second base assembly 720 to move with respect to the first base assembly 710. Because the first base assembly 710 engages the first handle component and the second base assembly 720 engages the second handle component, the second handle component longitudinally translates with respect to the first handle component, and this motion is imparted upon a steerable distal end portion of the delivery system. For example, turning the knob of the translation assembly 730 in a first direction causes the steerable distal end portion of the delivery system to move in a first direction, and turning the knob in a second direction causes the steerable distal end portion to move in a second direction different from (e.g., opposite to) the first direction.

Figure 8:
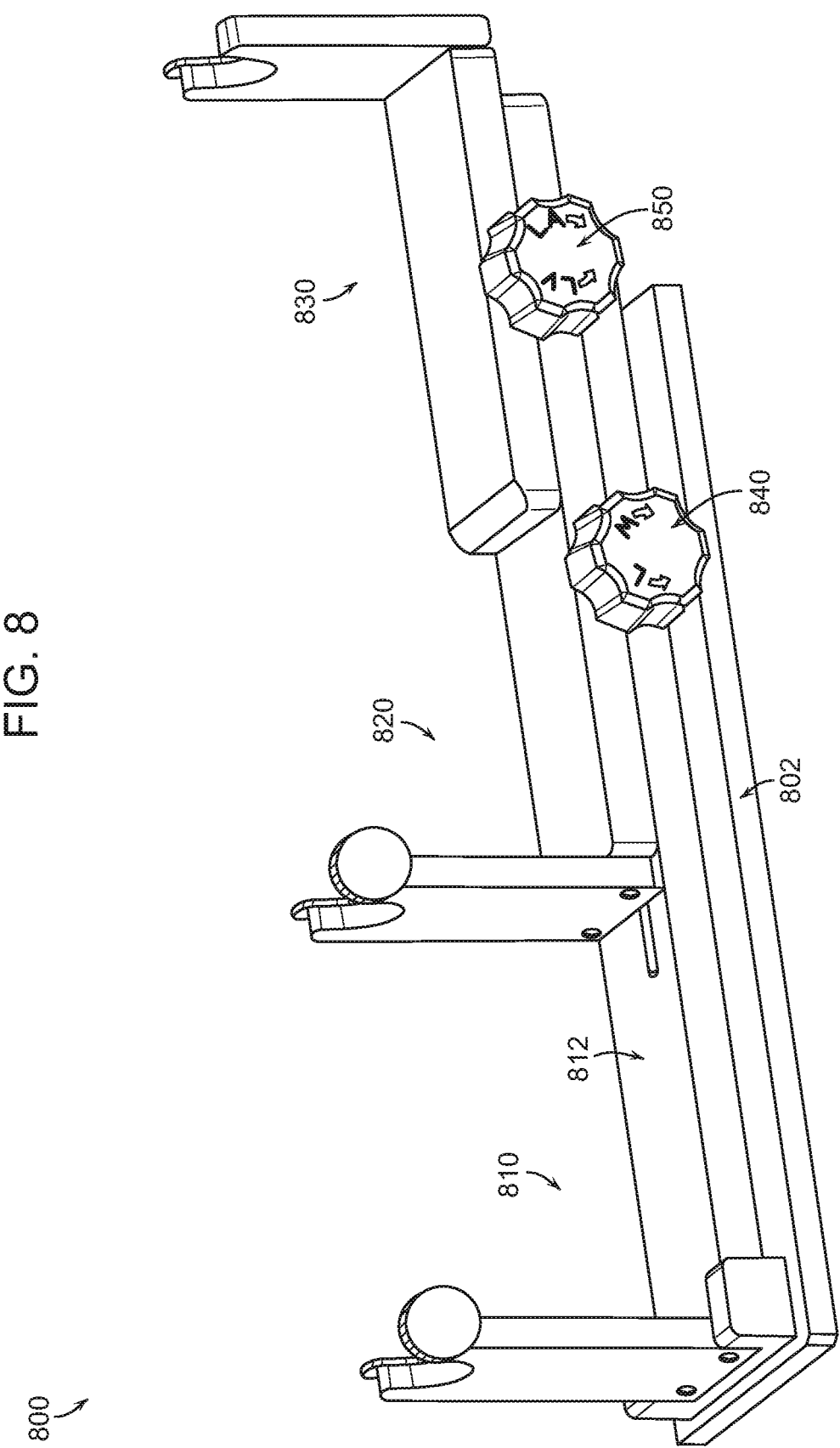
FIG. 8 is an isometric view of a support device configured in accordance with some examples of the present disclosure.

As shown in FIG. 8, the support device 800 can include a platform 802, a first base assembly 810, a second base assembly 820, a third base assembly 830, a first translation assembly 840, and a second translation assembly 850. Rather than the base assemblies 810, 820, 830 forming an acute angle with respect to the platform 802, the platform 802 is substantially parallel to the base portion 812 of the first base assembly 810 (i.e., the platform axis is substantially parallel to the longitudinal axis of the base assemblies). This may be achieved, for example, by excluding the spacer component 660 from the example shown in FIG. 6A such that the platform 802 and the first base portion 812 of the first base assembly 810 are in apposition. Alternatively, some examples may include a second spacer component configured to space apart the first end portion of the platform 802 from the first terminus of the first base portion 812. In such examples, the second spacer component may be substantially the same height as the first spacer component such that the base assemblies 810, 820, 830 and the platform 802 are spaced apart from each other and the platform axis is substantially parallel to the base assembly axis. This configuration may be particularly suitable for implanting devices (e.g., prosthetic heart valves) at the tricuspid valve and/or other delivery sites that do not benefit from a steep angle of approach.

Figure 9A:
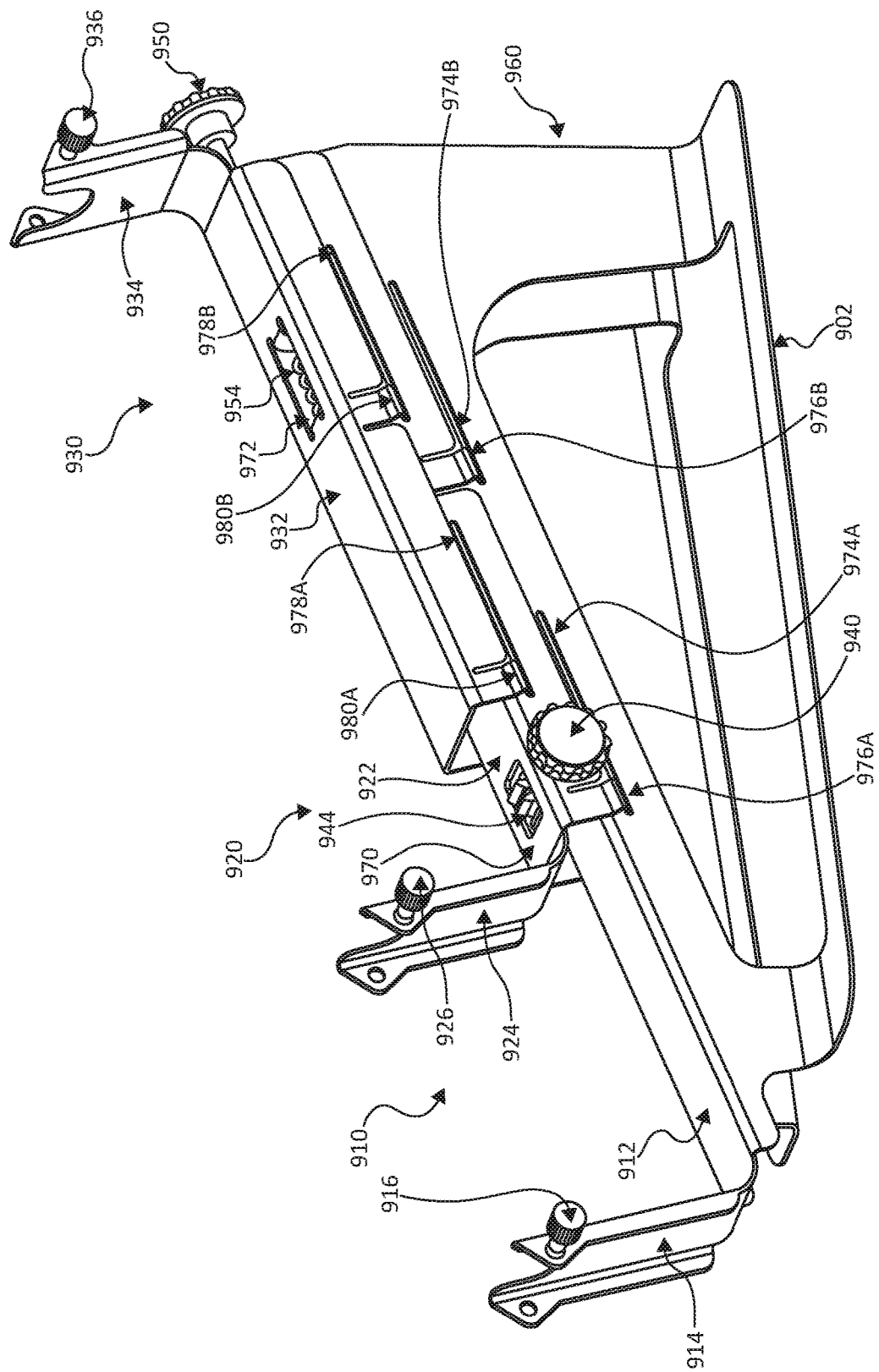
FIG. 9A is an isometric view of a support device configured in accordance with some examples of the present disclosure.
Figure 9B:
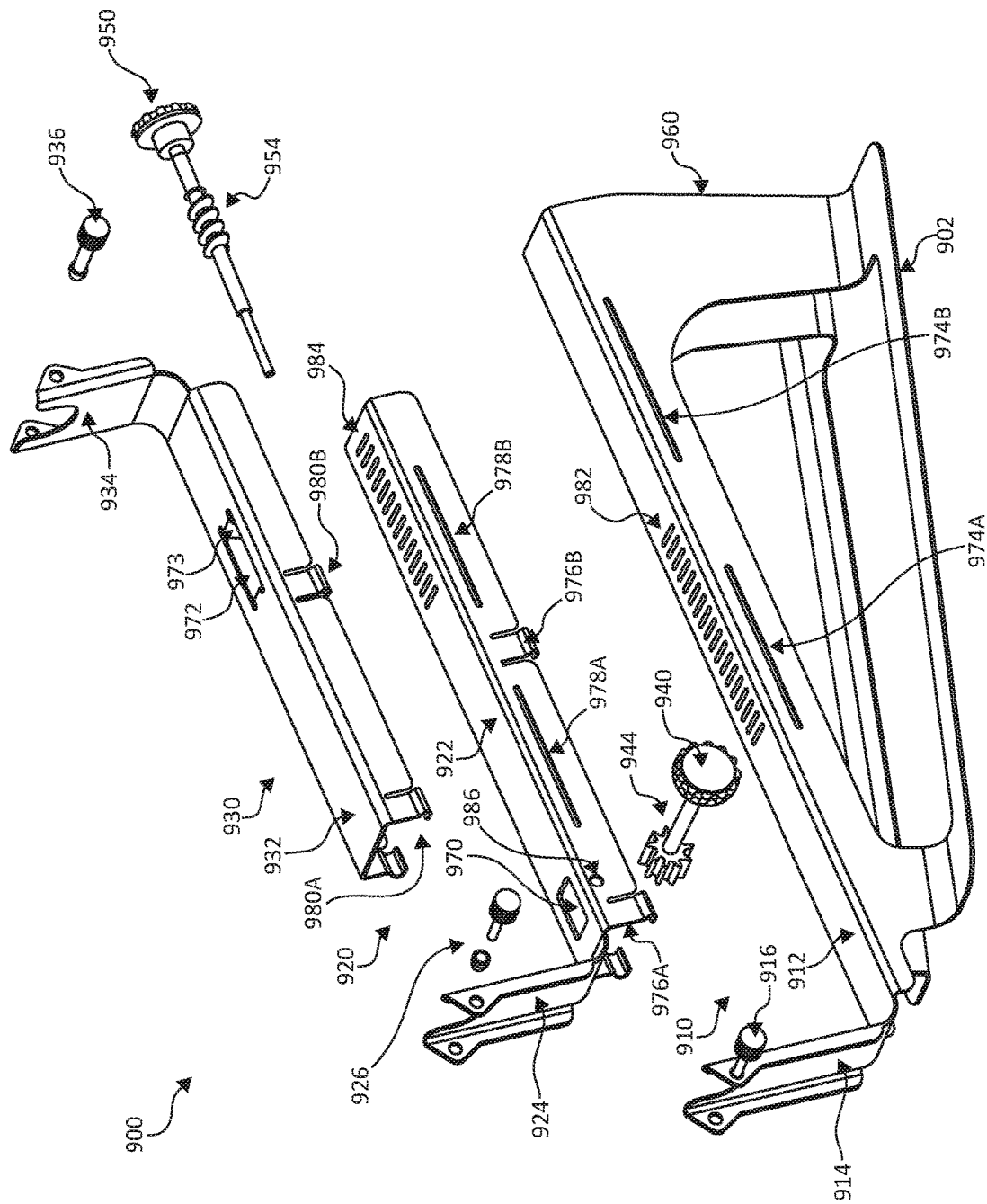
FIG. 9B is an exploded isometric view of the support device of FIG. 9A.

Referring to FIGS. 9A and 9B, an example support device 900 includes a platform 902, which includes a first end portion and a second end portion. The support device 900 also includes a first base assembly 910 including a first base portion 912 and a first support 914 configured to engage a first handle component of a delivery system handle. The support device 900 further includes a second base assembly 920 including a second base portion 922 and a second support 924 configured to engage a second handle component of the delivery system handle, and a third base assembly 930 including a third base portion 932 and a third support 934 configured to engage a third handle component of the delivery system handle. The first, second, and third supports 914, 924, and 934 extend in a direction away from the first base portion 912, the second base portion 922, and the third base portion 932, respectively. The first, second, and third supports 914, 924, and 934 include fasteners 916, 926, and 936, respectively, which are configured to secure the delivery system handle to support device 900.

The support device 900 further includes a first translation assembly 940 operably coupled to the first and second base assemblies 910 and 920. The first translation assembly 940 is configured to slidably translate the second base assembly 920 with respect to the first base assembly 910. To facilitate this, in some examples, the first translation assembly 940 may include a rack 982, a pinion 944, and a knob (as described above with respect to FIG. 6B). The pinion 944 may be operably coupled to both the rack 982 and the knob, for instance by a shaft, such that manipulating the knob causes the pinion 944 to rotate and thus causes the pinion 944 to longitudinally translate with respect to the rack 982. The rack 982 may be integral with or otherwise connected to the first base assembly 910 (e.g., may include spaced apart apertures defined in first base portion 912) such that this longitudinal translation causes the first base portion 912 and the second base portion 922 to move relative to each other (e.g., the second base portion 922 to move relative to a substantially stationary first base portion 912). In some examples, the shaft connecting the pinion 944 and the knob extends through an aperture 986 defined in the second base portion 922 to retain the pinion 944, the shaft, and the knob in position relative to the second base portion 922. In the example of FIGS. 9A and 9B, the second base portion 922 defines an aperture 970 through which the pinion 944 is visible or protrudes, which also may help maintain the position of the pinion 944, the shaft, and the knob.

In other examples, the first translation assembly 940 may be configured oppositely with respect to the first base portion 912 and the second base portion 922. For example, the rack 982 may be part of or formed in the second base portion 922, and the apertures 970 and 986 may be defined in the first base portion 912. Such an arrangement will cause similar relative longitudinal movement of the first base portion 912 and the second base portion 922.

The support device 900 also includes a second translation assembly 950 operably coupled to the second and third base assemblies 920 and 930. The second translation assembly 950 is configured to slidably translate the third base assembly 930 with respect to the second base assembly 920. To facilitate this, the second translation assembly 930 may include a worm gear 954, a plurality of apertures 984 defined in second base portion 922, and a knob. The worm gear 954 may be operably coupled to both the plurality of apertures 984 and the knob, such that manipulating the knob causes the work gear 954 to rotate and thus causes the worm gear 954 to longitudinally translate with respect to the plurality of apertures 984. The plurality of apertures 984 may be integral with the second base assembly 920 (e.g., may include spaced apart apertures defined in the second base portion 922) such that this longitudinal translation causes the second base portion 922 and the third base portion 932 to move relative to each other (e.g., the third base portion 932 to move relative to the second base portion 922).

In the example of FIGS. 9A and 9B, the third base portion 932 defines an aperture 972 through which the worm gear 954 is visible or protrudes. The third base portion 932 also may include tabs 973 (e.g., adjacent to aperture 972) that are configured to maintain the position of the worm gear 954 relative to the third base portion 932.

In other examples, the second translation assembly 950 may be configured oppositely with respect to the second base portion 922 and the third base portion 932. For example, plurality of apertures 984 may be part of or formed in the third base portion 932, and the aperture 972 and tabs 973 may be defined in the second base portion 922. Such an arrangement will cause similar relative longitudinal movement of the second base assembly 920 and the third base assembly 930. By having the knobs of the first translation assembly 940 and the second translation assembly 950 on different sides of the support device 900, the first translation assembly 940 and the second translation assembly 950 may be more easily differentiated by a clinician during use of the support device 900.

The support device 900 also includes features for restraining movement of the second base assembly 920 relative to the first base assembly 910 and restraining movement of the third base assembly 930 relative to the second base assembly 920. For example, the features may substantially prevent movement of the base assemblies 910, 920, and 930 relative to each other in directions other than the longitudinal direction. In the example of FIGS. 9A and 9B, the features restraining movement of the second base assembly 920 relative to the first base portion 910 and restraining movement of the third base assembly 930 relative to the second base assembly 920 include slots 974A and 974B in the first base portion 912 and corresponding tabs 976A and 976B in the second base portion 922. The tabs 976A and 976B are configured to mate within the slots 974A and 974B, allowing longitudinal movement of the second base assembly 920 relative to the first base assembly 910, while reducing or substantially preventing relative movement in other directions. Similarly, the second base portion 922 may include slots 978A and 978B in which tabs 980A and 980B of the third base portion 932 mate. Although the slots 974A and 974B and the corresponding tabs 976A and 976B are labelled on only the side shown in FIG. 9A, in some examples, similar slots and tabs are present on the opposite side of the support device 900.

The support device 900 may also include a spacing component 960 that separates the second end portion of the platform 902 from at least a portion of the first base assembly 910 (and also the second base assembly 920 and the third base assembly 930).

The first base portion 912, the second base portion 922, and the third base portion 932, as well as other base portions and other portions of support devices described herein, may be formed from any suitable material. For example, the first base portion 912, the second base portion 922, and the third base portion 932 may be formed from metal, plastic, or the like. In some implementations, the first base portion 912, the second base portion 922, and the third base portion 932 may be formed from folded sheet metal, such as folded stainless steel, tin, aluminum, titanium, or the like.

Figure 10A:
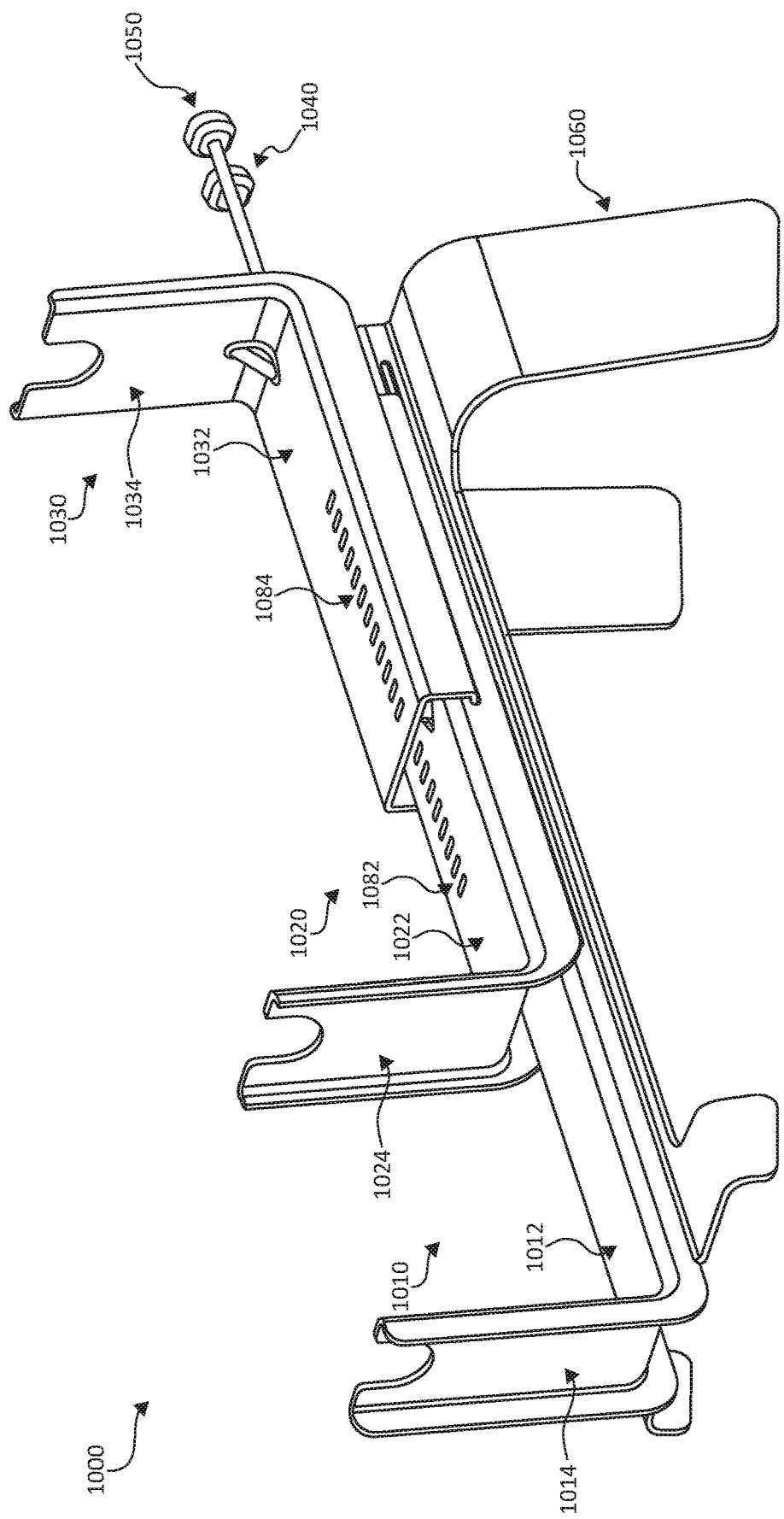
FIG. 10A is an isometric view of a support device configured in accordance with some examples of the present disclosure.
Figure 10B:
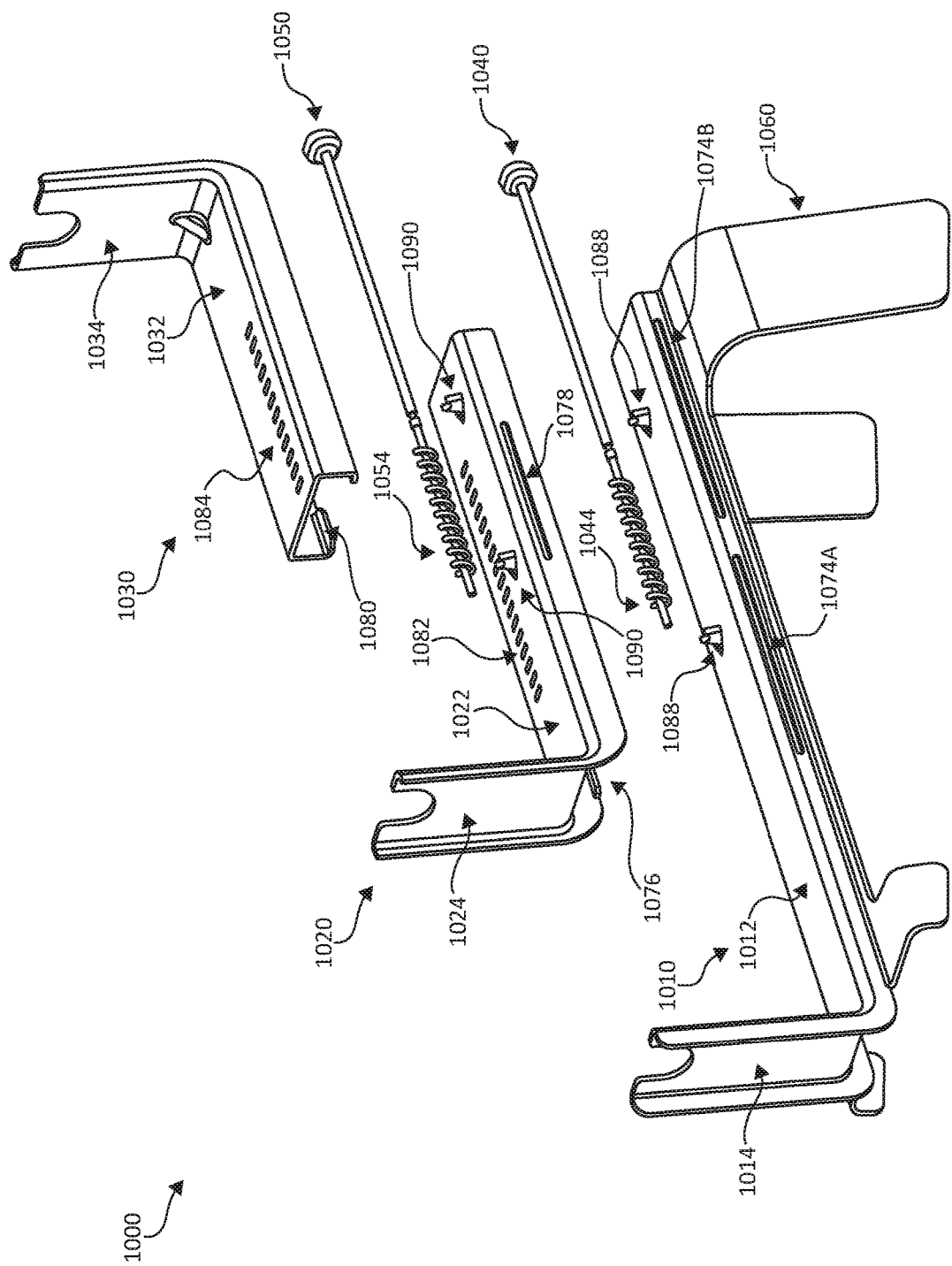
FIG. 10B is an exploded isometric view of the support device of FIG. 10A.

FIGS. 10A and 10B illustrate an example support device 1000. Like the support device 900, the support device 1000 includes a first base assembly 1010, a second base assembly 1020, and a third base assembly 1030. The first base assembly 1010 includes a first base portion 1012 and a first support 1014. The second base assembly 1020 includes a second base portion 1022 and a second support 1024. The third base assembly 1030 includes a third base portion 1032 and a third support 1034. The support device 1000 also includes a spacing component 1060.

Unlike the support device 900, which includes a first translation assembly 940 including a rack and pinion, the support device 1000 includes two translation assemblies including worm gears. The first translation assembly 1040 is operatively coupled to the first base assembly 1010 and the second base assembly 1020 and includes a first handle, a first worm gear 1044, and a first plurality of apertures 1082 defined in second base portion 1022. In the example of FIGS. 10A and 10B, the shaft of the first translation assembly 1040 is received by tabs 1088 formed by or attached to the first base portion 1012, which maintain the position of the worm gear 1044 relative to the first base assembly 1010. In other examples, the configuration of the first translation assembly 1040 may be switched with respect to the first base assembly 1010 and the second base assembly 1020. For instance, the tabs 1088 may be formed by or attached to the second base portion 1022 and the first plurality of apertures 1082 may be defined in the first base portion 1012.

The support device 1000 also includes a second translation assembly 1050. The second translation assembly 1050 is operatively coupled to the second base assembly 1020 and the third base assembly 1030 and includes a second handle, a second worm gear 1054, and a second plurality of apertures 1084 defined in the third base portion 1032. In the example of FIGS. 10A and 10B, the shaft of second translation assembly 1050 is received by tabs 1090 formed by or attached to the second base portion 1022, which maintain the position of the second worm gear 1054 relative to the second base assembly 1020. In other examples, the configuration of the second translation assembly 1050 may be switched with respect to the second base assembly 1020 and the third base assembly 1030. For instance, the tabs 1090 may be formed by or attached to the third base portion 1032 and the second plurality of apertures 1084 may be defined in the second base portion 1022.

The support device 1000 also includes features for restraining movement of the second base assembly 1020 relative to the first base assembly 1010 and restraining movement of the third base assembly 1030 relative to the second base assembly 1020. In the example of FIGS. 10A and 10B, the features restraining movement of the second base assembly 1020 relative to the first base portion 1010 include slots 1074A and 1074B in the first base portion 1012 and corresponding tabs 1076 in the second base portion 1022. The tabs 1076 mate within the slots 1074A and 1074B, allowing longitudinal movement of the second base assembly 1020 relative to the first base assembly 1010, while reducing or substantially preventing relative movement in other directions. Similarly, the second base portion 1022 may include a slot 978 in which a tab 1080 of third base portion 1032 mates in order to restrain movement of the third base assembly 1030 relative to the second base assembly 1020.

The first base portion 1012, the second base portion 1022, and the third base portion 1032 may be formed from any suitable material. For example, the first base portion 1012, the second base portion 1022, and the third base portion 1032 may be formed from metal, plastic, or the like. In some implementations, the first base portion 1012, the second base portion 1022, and the third base portion 103 may be formed from folded sheet metal, such as folded stainless steel, tin, aluminum, titanium, or the like.

Figure 11:
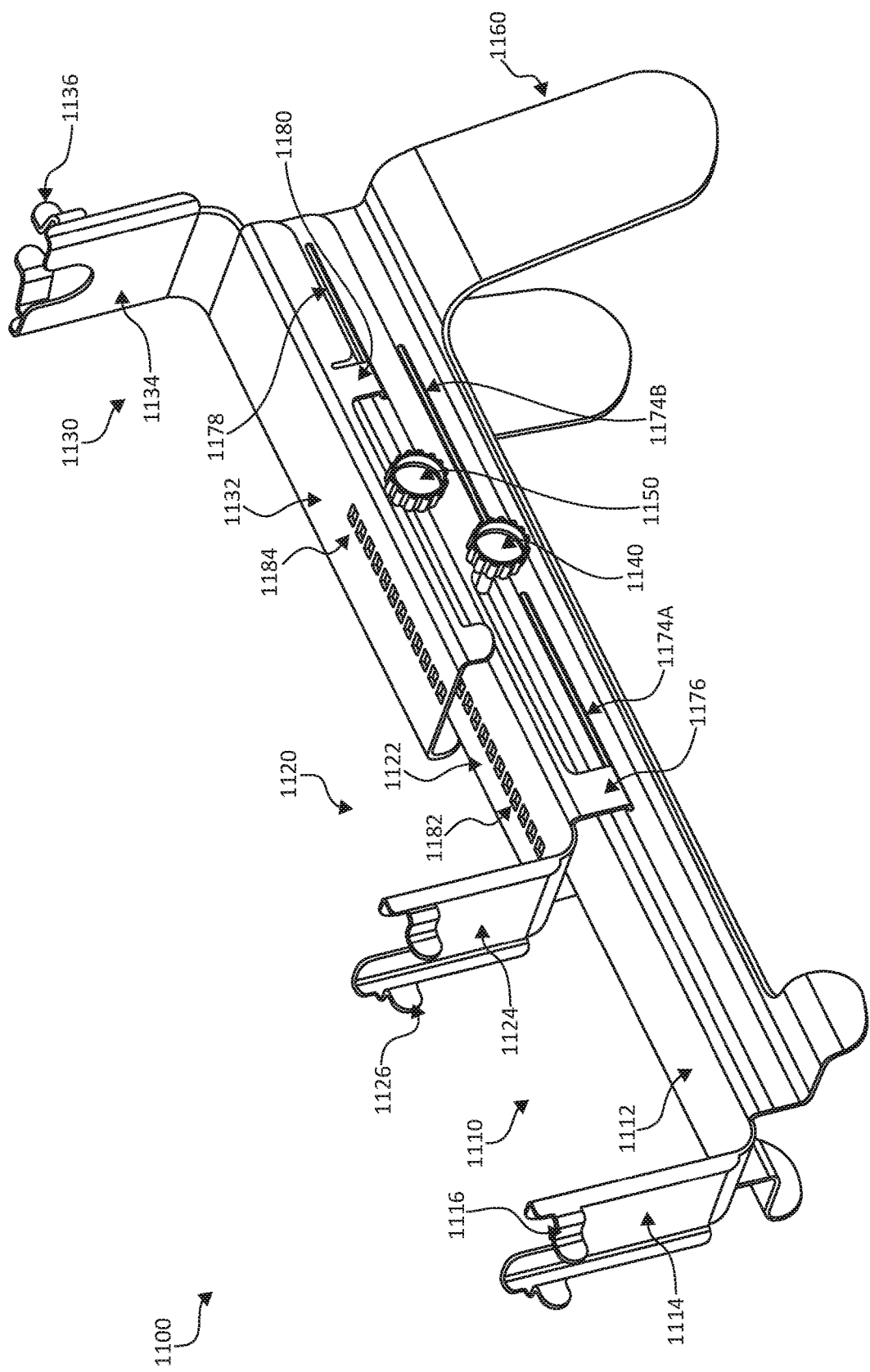
FIG. 11 is an isometric view of a support device configured in accordance with some examples of the present disclosure.

FIG. 11 illustrates another example support device 1100. Like the support device 1000, the support device 1100 includes a first base assembly 1110, a second base assembly 1120, and a third base assembly 1130. The first base assembly 1110 includes a first base portion 1112 and a first support 1114. The second base assembly 1120 includes a second base portion 1122 and a second support 1124. The third base assembly 1130 includes a third base portion 1132 and a third support 1134. The support device 1100 also includes a spacing component 1160.

Unlike the support device 1000, each of the first and second translation assemblies 1140 and 1150 including rack and pinion gears. The first translation assembly 1140 is operatively coupled to the first base assembly 1110 and the second base assembly 1120 and includes a first handle, a first pinion (not shown in FIG. 11), and a first rack 1182 defined in the second base portion 1122. The first rack 1182 is integral with the second base portion 1122 and includes a plurality of apertures defined in the second base portion

1122. In other examples, the configuration of the first translation assembly 1140 may be switched with respect to the first base assembly 1110 and the second base assembly 1120. For instance, the rack 1182 may be defined in the first base portion 1112.

The second translation assembly 1150 is operatively coupled to the second base assembly 1120 and the third base assembly 1130 and includes a second handle, a second pinion (not shown in FIG. 11), and a second rack 1184 defined in the third base portion 1132. In other examples, the configuration of the second translation assembly 1150 may be switched with respect to the second base assembly 1120 and the third base assembly 1130. For instance, the rack 1184 may be defined in the second base portion 1122.

The support device 1100 also includes features for restraining movement of the second base assembly 1120 relative to the first base assembly 1110 and restraining movement of the third base assembly 1130 relative to the second base assembly 1120. In the example of FIG. 11, the features restraining movement of the second base assembly 1120 relative to the first base portion 1110 include slots 1174A and 1174B in first base portion 1112 and corresponding tabs 1176 in the second base portion 1122. The tabs 1176 mate within the slots 1174A and 1174B, allowing longitudinal movement of the second base assembly 1120 relative to the first base assembly 1110, while reducing or substantially preventing relative movement in other directions. Similarly, the second base portion 1122 may include a slot 1178 in which a tab 1180 of the third base portion 1132 mates in order to restrain movement of the third base assembly 1130 relative to the second base assembly 1120.

The first base portion 1112, the second base portion 1122, and the third base portion 1132 may be formed from any suitable material. For example, the first base portion 1112, the second base portion 1122, and the third base portion 1132 may be formed from metal, plastic, or the like. In some implementations, the first base portion 1112, the second base portion 1122, and the third base portion 1132 may be formed from folded sheet metal, such as folded stainless steel, tin, aluminum, titanium, or the like.

Figure 12:
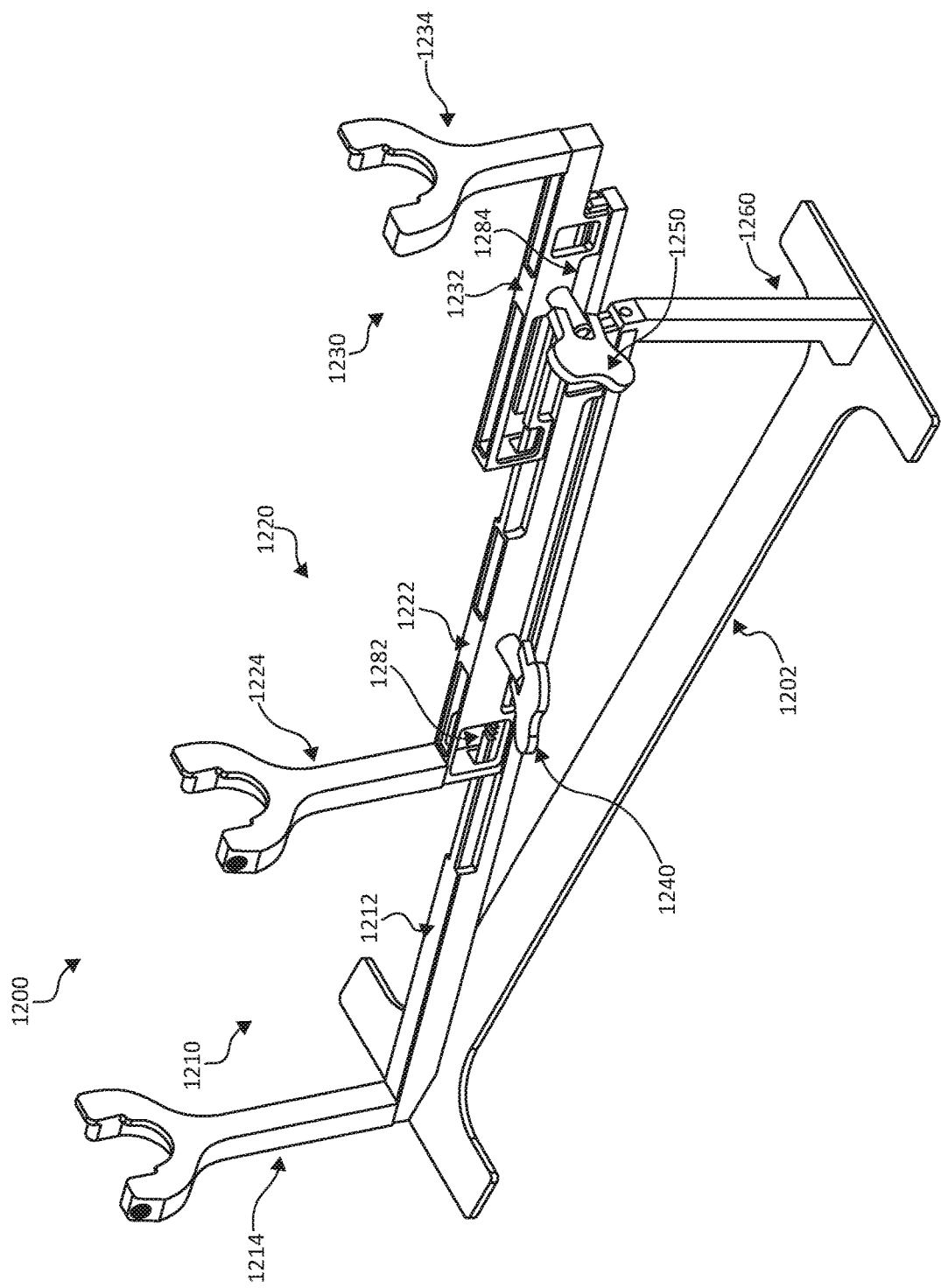
FIG. 12 is an isometric view of a support device configured in accordance with some examples of the present disclosure.

FIG. 12 illustrates another example support device 1200. Like the support device 1000, the support device 1200 includes a first base assembly 1210, a second base assembly 1220, and a third base assembly 1230. The first base assembly 1210 includes a first base portion 1212 and a first support 1214. The second base assembly 1220 includes a second base portion 1222 and a second support 1224. The third base assembly 1230 includes a third base portion 1232 and a third support 1234. The support device 1200 also includes a spacing component 1260 and a platform 1202, which is configured to rest on a surface, such as a floor, a stool, a table, or the like.

The support device 1200 further includes first and second translation assemblies 1240 and 1250. Unlike the support device 1000, each of the first and second translation assemblies 1240 and 1250 including rack and pinion gears, like the support device 1100. However, rather than knobs, the first and second translation assemblies 1240 and 1250 include handles with dual lobes. Further, the racks 1282 and 1284 include spaced apart protrusions defined in surfaces of the first base portion 1212 and the second base portion 1222, respectively. In other examples, the configurations of the first and second translation assemblies 1240 and 1250 may be switched with respect to the base assemblies 1210, 1220, and 1230. For instance, the rack 1282 may be defined in the second base portion 1222 and the rack 1284 may be defined in the third base portion 1232.

Figure 13A:
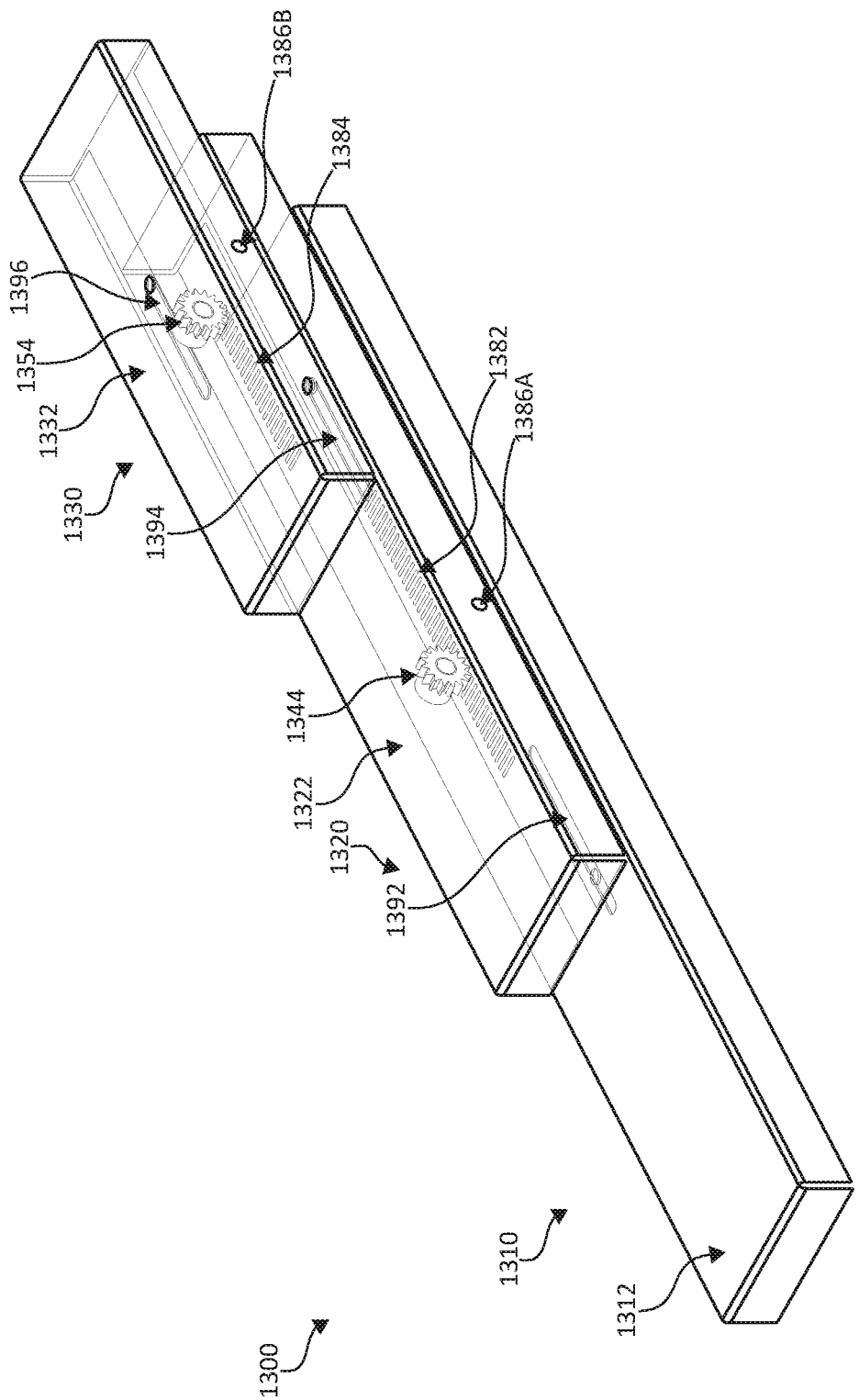
FIG. 13A is an isometric view of a support device configured in accordance with some examples of the present disclosure.
Figure 13B:
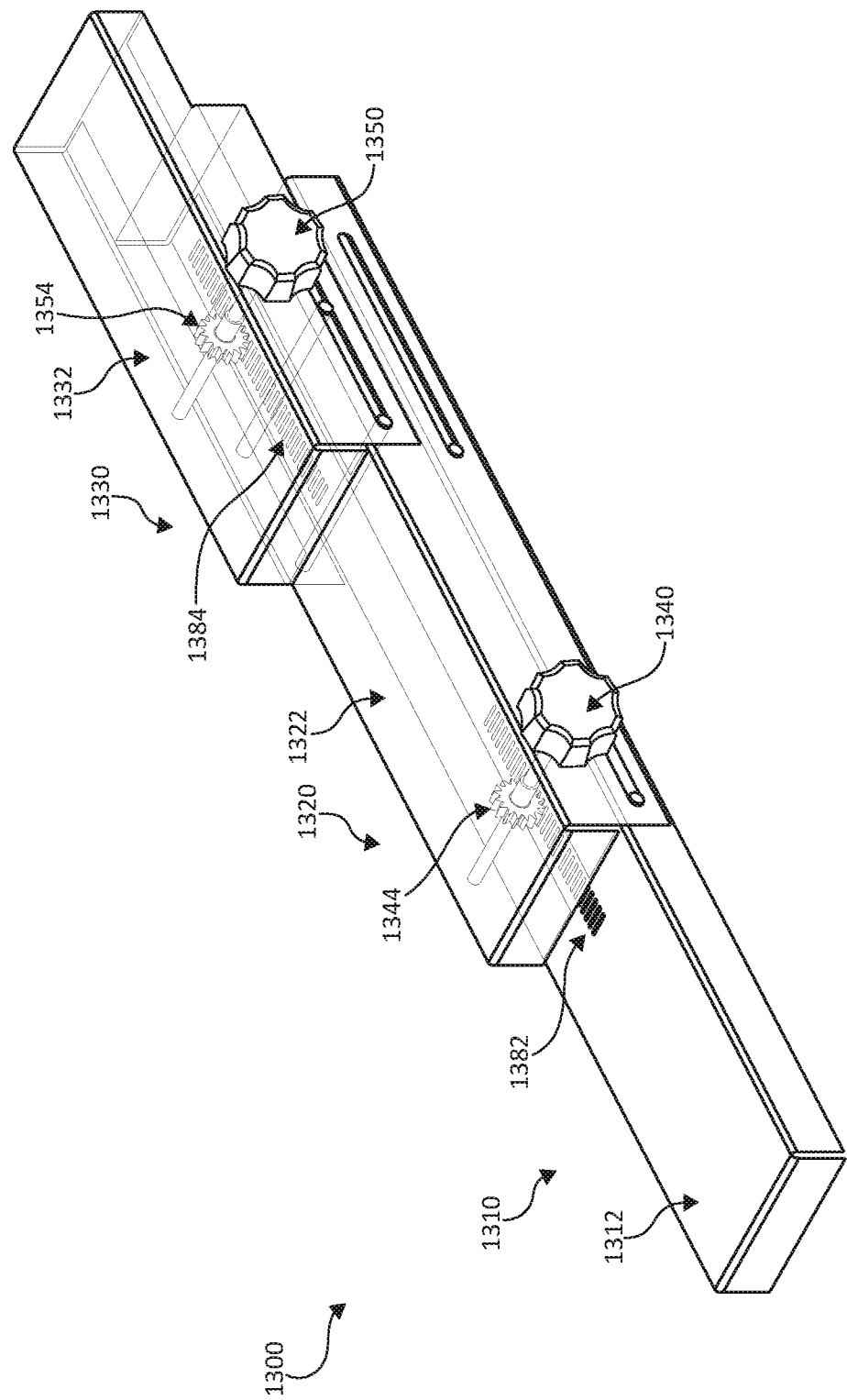
FIG. 13B is another isometric view of a support device of FIG. 13A.

FIGS. 13A and 13B illustrate a portion of another example support device 1300. Like the support device 1000, the support device 1300 includes a first base assembly 1310, a second base assembly 1320, and a third base assembly 1330. The first base assembly 1310 includes a first base portion 1312, and may include a first support, which is not shown in FIGS. 13A and 13B. The second base assembly 1320 includes a second base portion 1322, and may include a second support, which is not shown in FIGS. 13A and 13B. The third base assembly 1330 includes a third base portion 1332, and may include a third support, which is not shown in FIGS. 13A and 13B.

The support device 1300 includes first and second translation assemblies for translating movement of the bases relative to each other. Each of the first and second translation assemblies including rack and pinion gears. As shown in FIGS. 13A and 13B, the first translation assembly is operatively coupled to the first base assembly 1310 and the second base assembly 1320 and includes a first handle 1340, a first pinion 1344, and a first rack 1382 defined in the first base portion 1312. The first rack 1382 is integral with the first base portion 1312 and includes a plurality of apertures defined in the first base portion 1312. In other examples, the configuration of the first translation assembly may be switched with respect to the first base assembly 1310 and the second base assembly 1320. For instance, the rack 1382 may be defined in the second base portion 1322.

The second translation assembly is operatively coupled to the second base assembly 1320 and the third base assembly 1330 and includes a second handle 1350, a second pinion 1354, and a second rack 1384 defined in the second base portion 1322. In other examples, the configuration of the second translation assembly may be switched with respect to the second base assembly 1320 and the third base assembly 1330. For instance, the rack 1384 may be defined in the third base portion 1332.

The support device 1100 also includes features for restraining movement of the second base assembly 1320 relative to the first base assembly 1310 and restraining movement of the third base assembly 1330 relative to the second base assembly 1320. In the example of FIGS. 13A and 13B, the features restraining movement of second base assembly 1320 relative to first base portion 1310 include a slot 1392 in the first base portion 1312 and a corresponding tab, pin, screw, or bolt coupled to the second base portion 1322 and extending through the slot 1392. Similarly, the second base portion 1322 may define a slot 1394 and/or 1396 and a corresponding tab(s), pin(s), screw(s), or bolt(s) coupled to the third base portion 1332 and extending through the slot(s) 1392 and/or 1396.

The first base portion 1312, the second base portion 1322, and the third base portion 1332 may be formed from any suitable material. For example, the first base portion 1312, the second base portion 1322, and the third base portion 1332 may be formed from metal, plastic, or the like. In some implementations, the first base portion 1312, the second base portion 1322, and the third base portion 1332 may be formed from folded sheet metal, such as folded stainless steel, tin, aluminum, titanium, or the like.

Figure 14:
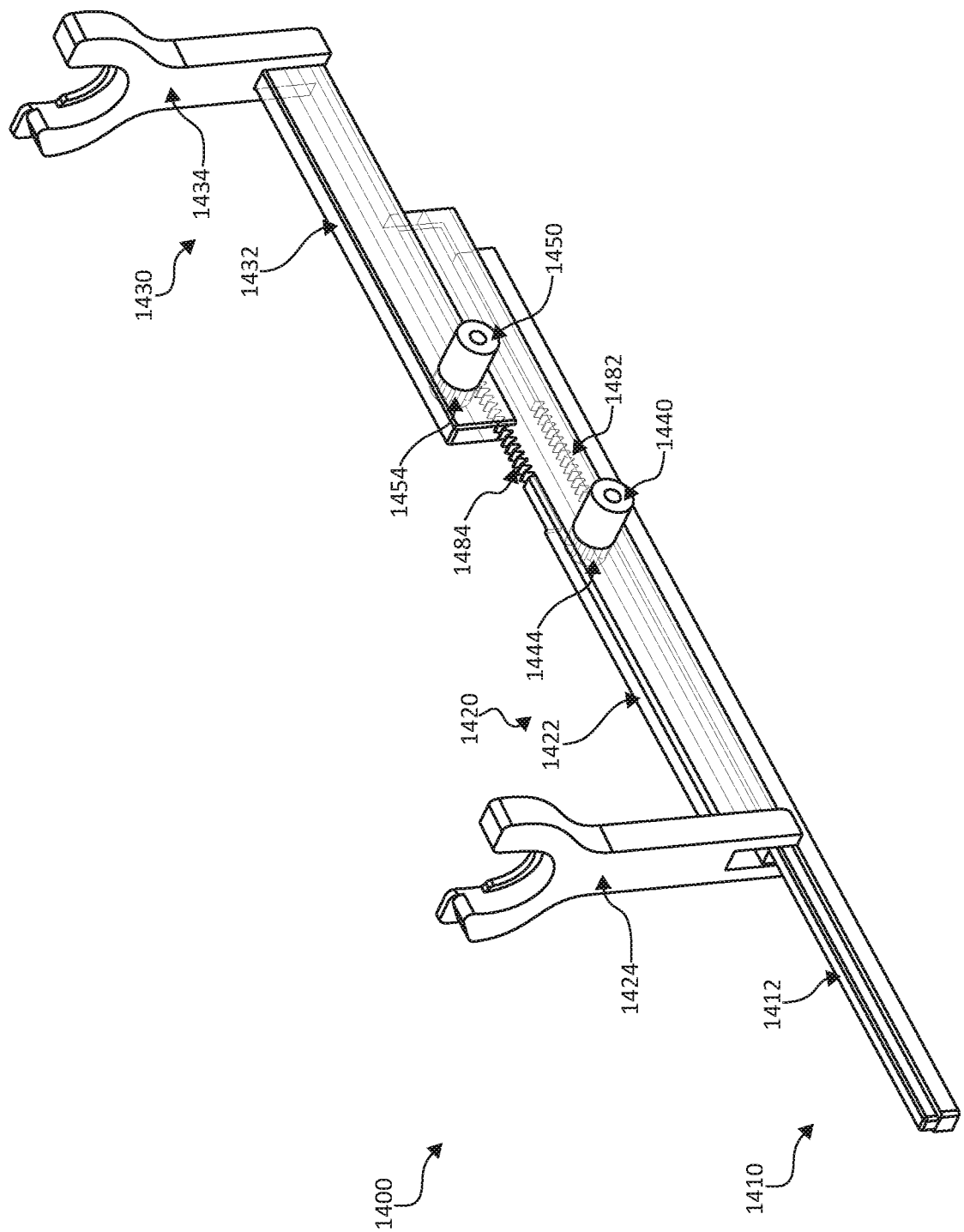
FIG. 14 is an isometric view of a support device configured in accordance with some examples of the present disclosure.

FIG. 14 illustrates a portion of another example support device 1400. The support device 1400 includes a first base assembly 1410, a second base assembly 1420, and a third base assembly 1430. The first base assembly 1410 includes a first base portion 1412, and may omit a first support. The second base assembly 1420 includes a second base portion 1422 and a second support 1424. The third base assembly 1430 includes a third base portion 1432 and a third support 1434.

The support device 1400 also includes first and second translation assemblies 1440 and 1450 configured to translate the base assemblies 1410, 1420, and 1430 relative to each other. Each of the first and second translation assemblies 1440 and 1450 including rack and pinion gears. As shown in FIG. 14, the first translation assembly 1440 is operatively coupled to the first base assembly 1410 and the second base assembly 1420 and includes a first handle, a first pinion 1444, and a first rack 1482 defined in the first base portion 1412. The first rack 1482 is integral with the first base portion 1412 and includes a plurality of protrusions extending from first base portion 1412. In other examples, the configuration of the first translation assembly 1440 may be switched with respect to the first base assembly 1410 and the second base assembly 1420. For instance, the rack 1482 may be defined in the second base portion 1422.

The second translation assembly 1450 is operatively coupled to the second base assembly 1420 and the third base assembly 1430 and includes a second handle, a second pinion 1454, and a second rack 1484 defined in the second base portion 1422. In other examples, the configuration of the second translation assembly 1450 may be switched with respect to the second base assembly 1420 and the third base assembly 1430. For instance, the rack 1484 may be defined in the third base portion 1432.

The first base portion 1412, the second base portion 1422, and the third base portion 1432 may be formed from any suitable material. For example, the first base portion 1412, the second base portion 1422, and the third base portion 1432 may be formed from metal, plastic, or the like. In some implementations, the first base portion 1412, the second base portion 1422, and the third base portion 1432 may be formed from stainless steel, tin, aluminum, titanium, or the like.

Any of the support devices 600-1400 described herein may be made of materials suitable for use in an operating room or medical facility. For example, suitable materials may include, but are not limited to, plastics, polymers, composites, thermoplastics, stainless steel, sheet metal, titanium, aluminum, and the like. For example, in one example, certain aspects of the support device (e.g., the platform and base assemblies) may be made of a thermoplastic acetal resin (e.g., Delrin® available from DuPont of Wilmington, Delaware). And in some examples, certain aspects of the support device (e.g., the rack and pinion) may be made of stainless steel. The support devices described herein may be disposable after one or more uses (i.e., suitable for one use then disposable, suitable for two uses then disposable, suitable for three uses then disposable, etc.), or may be suitable for continued reuse. In some instances, the materials may be compatible with hospital reuse protocols, including cleaning, sterilization, use of an autoclave, of the like.

Furthermore, the support devices 600-1400 described herein may be adjustable between an in-use configuration and a transportation configuration. The in-use configuration may be substantially similar to the configurations described above with respect to FIGS. 6A-14. In the transportation configuration, the support device may be folded flat or otherwise configured so as to occupy less space. For example, the support device may take on a transportation configuration by removing screws coupling the spacing component (e.g., the spacing component 660 in FIGS. 6A-6C) to the platform and the base assemblies and/or removing screws coupling the base portions to the supports. In another example, the base assemblies may include a hinged connection between the base portion and the support such that they may be folded together to occupy less space. The device can be quickly transformed between the in-use and transportation configurations by, for example, using the same or different screws to reassemble the device.

Figure 15A:
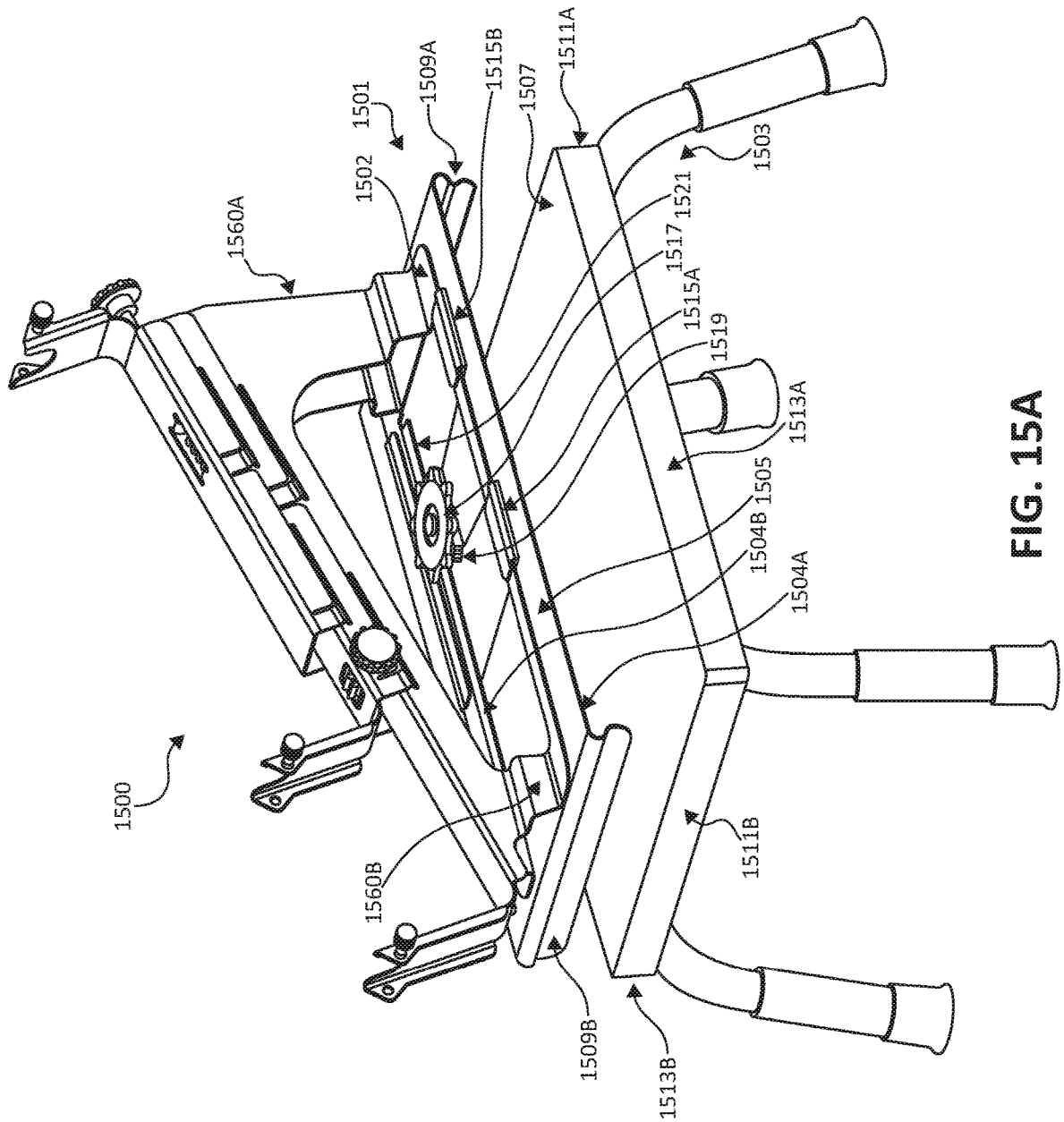
FIGS. 15A and 15B are isometric views of an example support device and an example coupling device.
Figure 15B:
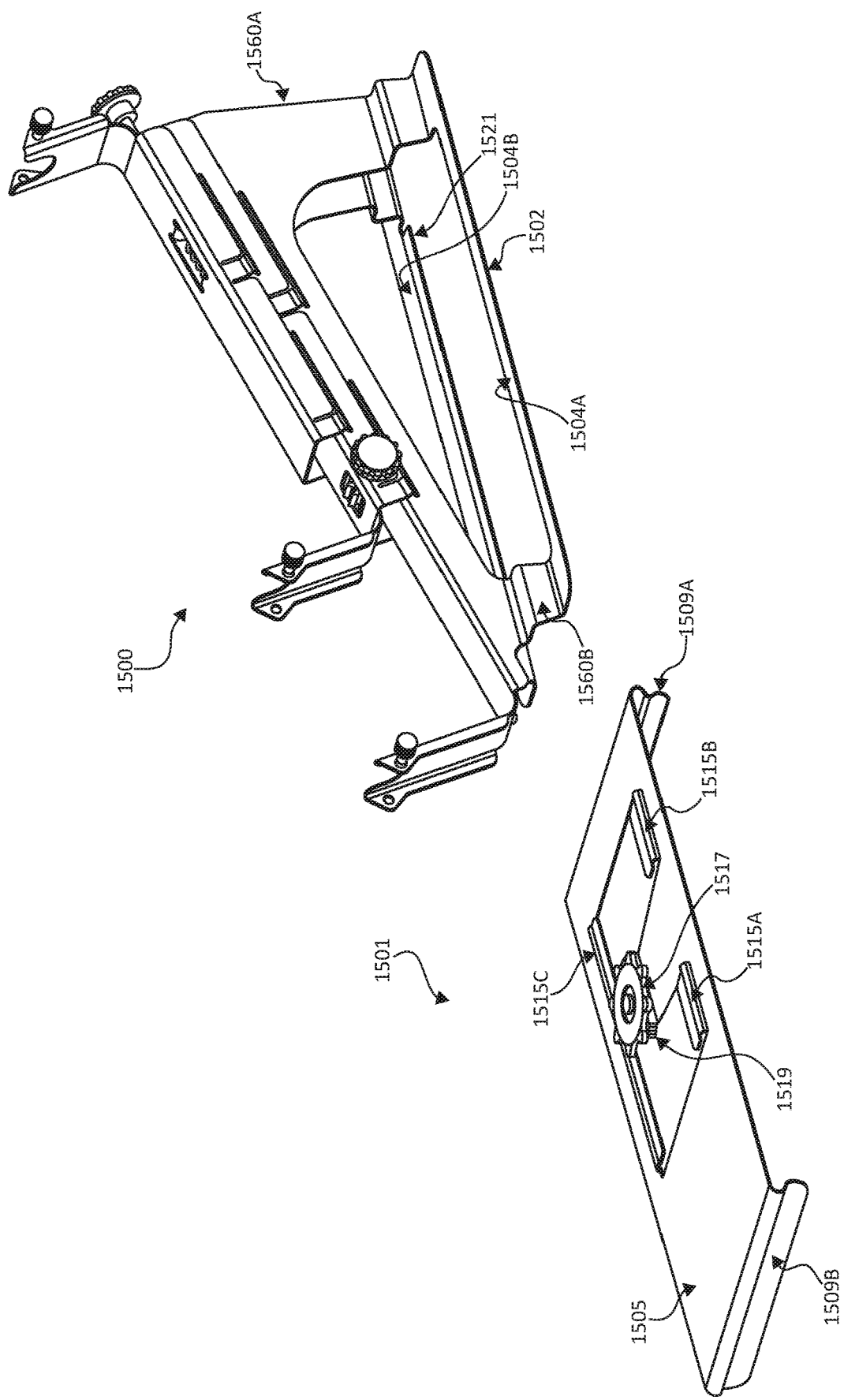

In some examples, a support device may be used with a coupling device configured to couple the support device to a supporting structure, such as a stool, table, or the like. FIGS. 15A and 15B isometric views of an example coupling device 1501 used with an example support device 1500 that is similar to the support device 900 of FIGS. 9A and 9B. Other coupling devices may have different configurations, e.g., to mate with support devices having different bases. Additionally, in some examples, a coupling device may be integral with a support device, e.g., may be an integral part of the base of the support device. As such, it will be understood that the principles described with reference to a coupling device 1501 in FIGS. 15A and 15B are also applicable to coupling devices that could be used with or integral with the support devices 600, 700, 800, 1000, 1100, 1200, 1300, and 1400 illustrated in FIGS. 6A-6D, 7, 8, 10A and 10B, 11, 12, 13A, 13B, and 14.

The system shown in FIGS. 15A and 15B includes a support device 1500 and a coupling device 1501. The support device 1500 is similar to the support device 900 of FIGS. 9A and 9B, aside from the differences described herein. Accordingly, all features of support device 1500 are not labelled for ease of description and clarity.

The support device 1500 includes a platform 1502. The platform 1502 extends from near a back end of support device 1500 to near a front end of support device 1500. The platform 1502 attaches to a first pair of supports 1560A at the back end of support device 1500 and a second pair of supports 1560B at or near the front end of support device 1500 (which can correspond to the side closest to a patient when the support device 1500 is in use during a medical procedure). The first and second pairs of supports 1560A and 1560B separate the remainder of the support device 1500 from the platform 1502 and define the angle of the delivery system handle(s) with respect to the platform 1502.

The platform 1502 also includes one or more features configured to engage with the coupling device 1501. In the example shown in FIGS. 15A and 15B the features include longitudinally extending bases 1504A and 1504B. The longitudinally extending base 1504A attaches to and extends from one of the first supports 1560A to one of the second supports 1560B. The longitudinally extending base 1504B attaches to and extends from the other of the first supports 1560A to the other of the second supports 1560B. In other examples, the one or more features configured to engage with the coupling device 1501 may be different, such as one or more transversely extending bases (e.g., a transversely extending base that extends laterally from one of the first supports 1560A to the other of the first supports 1506A and/or a transversely extending base that extends laterally from one of the second supports 1560B to the other of the second supports 1506V), one or more longitudinally or transversely extending flanges that do not connect two supports 1560A or 1560B, or the like.

The coupling device 1501 includes features configured to engage with a supporting structure, such as a stool, table, or the like to couple the support device 1500 to the supporting structure. In the example of FIGS. 15A and 15B, the supporting structure is a stool 1503. The coupling device 1501 may include one or more structural features configured to engage the supporting structure, such as a base 1505 and one or more flanges. The base 1505 is configured to engage (e.g., rest against) a major surface 1507 of the stool 1503. For instance, as shown in the example of FIG. 15A, the coupling device 1501 includes a first flange 1509A and a second flange 1509B, each of which extends from an end of the base 1505 and is configured to engage with a corresponding the vertical surface 1511A and 1511B of stool 1503. In some examples, the flanges 1509A and 1509B may be configured to engage the transverse vertical surfaces 1511A and 1511B of stool 1503 (as shown in FIG. 15A) to reduce or substantially prevent longitudinal movement of the coupling device 1501 relative to the stool 1503. Additionally, or alternatively, the coupling device 1501 may include flanges configured to engage the longitudinal vertical surfaces 1513A and 1513B of the stool 1503, which extend between the transverse surfaces 1511A and 1511B.

In some implementations, as shown in FIGS. 15A and 15B, the flanges 1509A and 1509B may include biasing features configured to improvement engagement between the flanges 1509A and 1509B and the transverse vertical surfaces 1511A and 1511B, respectively. The biasing features may include curved portions of the flanges 1595A and 1509B, the at-rest angle between the flanges 1509A and 1509B and the base 1505, or the like. Additionally, or alternatively, the surfaces of the flanges 1509A and 1509B that face transverse vertical surfaces 1511A and 1511B, respectively, may include one or more features that increase friction between the surfaces of the flanges 1509A and 1509B and the transverse vertical surfaces 1511A and 1511B. The features that increase friction may include, for example, a surface finish (e.g., increased surface roughness or knurling), a material on the surface (e.g., a foam, rubber, or the like), or the like.

The base 1505 also includes one or more structures configured to engage the support device 1500. For example, the base 1505 may include one or more clips or flanges 1515A, 1515B, and 1515C configured to accept or engage with the longitudinally extending bases 1504A and 1504B of support device 1500. The one or more clips or flanges 1515A, 1515B, and 1515C may be configured to restrict vertical and/or transverse movement of support device 1500 relative to coupling device 1501 while allowing longitudinal movement of support device 1500 relative to coupling device 1501. Although three clips or flanges 1515A, 1515B, and 1515C are shown in FIGS. 15A and 15B, in other examples, the base 1505 may include more or fewer clips or flanges, or may include other structures configured to engage the support device 1500, such as protrusions, depressions, channels, or the like.

The support device 1500 and the coupling device 1501 also together define a translation assembly configured to allow controlled longitudinal translation of the support device 1500 relative to the coupling device 1501. In the example shown in FIGS. 15A and 15B, the translation assembly includes a rack and pinion, with a pinion 1519 being attached to the coupling device 1501 and a rack 1521 being attached to or integral with the support device 1500. The pinion 1519 is also attached to a knob 1517 that allows a user to actuate the pinion 1519 to longitudinally translate the support device 1500 relative to the coupling device 1501. Translation of the support device 1500 ultimately allows longitudinal translation of the entire delivery system handle assembly, e.g., relative to the patient.

In other examples, the translation assembly defined by the support device 1500 and the coupling device 1501 may be configured differently. For example, the rack 1521 may be part of the base 1505 of the coupling device 1501 and the pinion 1519 may be attached to the support device 1500. As another example, a worm gear may be used (see, e.g., FIGS. 9A, 9B, 10A, and 10B) instead of a rack and pinion. In any case, the coupling device 1501 may provide improved retention of the support device 1500 relative to a support structure, such as the stool 1503, and may enable controlled longitudinal translation of the support device 1500 (and the delivery system handle assembly supported by support device 1500) relative to the patient.

Figure 16:
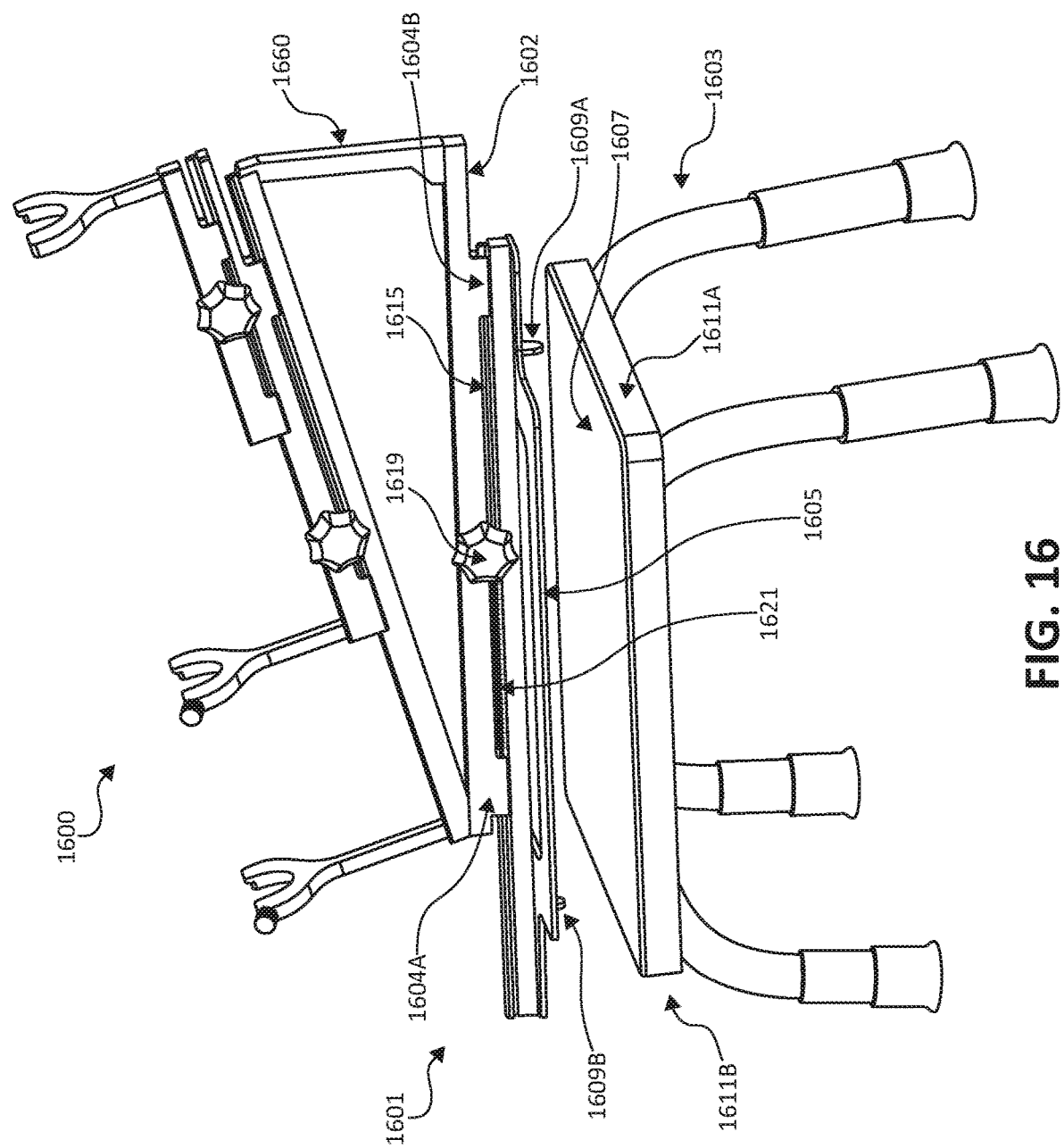
FIG. 16 is an isometric view of an example support device and an example coupling device.

FIG. 16 is an isometric view of another example coupling device 1601 used with an example support device 1600. The system shown in FIG. 16 includes a support device 1600 and a coupling device 1601. The support device 1600 is similar to support device 1200 of FIG. 12, aside from the differences described herein. Accordingly, all features of support device 1600 are not labelled for ease of description and clarity.

The support device 1600 includes a platform 1602, which extends from near a back end of support device 1600 to near a front end of support device 1600. The platform 1602 attaches to a support 1660 at the back end of support device 1600 is attached to a front end of platform 1602. A support 1660 separate the remainder of the support device 1600 from the platform 1602 and define the angle of the delivery system handle(s) with respect to the platform 1602.

The platform 1602 also includes one or more features configured to engage with the coupling device 1501. In the example shown in FIG. 16, the features include tabs 1604A and 1604B that fit within one or more channels 1615 of coupling device 1601. Although the tabs 1604A and 1604B are shown on only one side of the platform 1602, corresponding tabs also may be present on the opposite side of the platform 1602 not shown in FIG. 16.

The coupling device 1601 includes features configured to engage with a supporting structure, such as a stool, table, or the like to couple the support device 1600 to the supporting structure. In the example of FIG. 16, the supporting structure is a stool 1603. The coupling device 1601 may include one or more structural features configured to engage the supporting structure, such as a base 1605 one or more flanges. The base 1605 is configured to engage (e.g., rest against) a major surface 1607 of the stool 1603. For instance, the coupling device 1601 may include a first flange 1609A and a second flange 1609B, each of which extends from the base 1605 and is configured to engage with a corresponding vertical surface of the stool 1603. In some examples, the flanges 1609A and 1609B may be configured to engage transverse vertical surfaces 1611A and 1611B of the stool 1603 to reduce or substantially prevent longitudinal movement (in the direction extending between transverse vertical surfaces 1611A and 1611B) of the coupling device 1601 relative to stool 1603.

The base 1605 also includes one or more structures configured to engage the support device 1600. For example, the base 1605 may include one or more channels 1615 configured to accept or engage with the tabs 1604A and 1604B of the support device 1600. The one or more channels 1615 may be configured to restrict vertical and/or transverse movement (i.e., movement in the direction normal to surface 1607 of stool 1603 and in the direction parallel to transverse vertical surfaces 1611A and 1611B, respectively) of the support device 1600 relative to coupling device 1601 while allowing longitudinal movement (i.e., in the direction extending between transverse vertical surfaces 1611A and 1611B) of the support device 1600 relative to the coupling device 1601. Although one channel 1615 is shown in FIG. 16, the base 1605 may include a similar channel on the opposite side of the base 1605.

The support device 1600 and the coupling device 1601 also together define a translation assembly configured to allow controlled longitudinal translation of the support device 1600 relative to the coupling device 1601. In the example shown in FIG. 16, the translation assembly includes a rack and pinion, with a pinion being attached to the support device 1600 and a rack 1621 being attached to or integral with the coupling device 1601. The pinion is also attached to a knob 1617 that allows a user to actuate the pinion to longitudinally translate the support device 1600 relative to the coupling device 1601. Translation of the support device 1600 ultimately allows longitudinal translation of the entire delivery system handle assembly, e.g., relative to the patient.

In other examples, the translation assembly defined by the support device 1600 and the coupling device 1601 may be configured differently. For example, rack 1621 may be part of the support device 1600 and the pinion and knob 1619 may be attached to the coupling device 1601. As another example, a worm gear may be used (see, e.g., FIGS. 9A, 9B, 10A, and 10B) instead of a rack and pinion. In any case, the coupling device 1601 may provide improved retention of the support device 1600 relative to a support structure, such as stool 1603, and may enable controlled longitudinal translation of the support device 1600 (and the delivery system handle assembly supported by support device 1600) relative to the patient.

The present disclosure describes support devices suitable for use in delivering medical devices to the hearts of patients in need thereof and includes associated methods for delivering a medical device to the heart of a patient. For example, the support device may be used during a procedure to deliver and/or deploy a prosthetic mitral valve device to a mitral valve of a human heart. To do so, a clinician may position an introducer through vasculature into a space proximal to the septal wall or proximal to the right atrium. The clinician may then thread a delivery catheter system having a first catheter shaft and a second catheter shaft through the introducer and beyond. Once the distal end of the delivery catheter system is adjacent to the introducer, the clinician may place the delivery system handle into a support device described herein. Alternatively, the delivery system handle may be placed into the support device once the distal end of the delivery system is positioned adjacent to the mitral valve. Another alternative is to place the delivery system into the support device before the distal end of the delivery system reaches the introducer. For example, in one example, the entire procedure may be done with the delivery system handle in the support device.

Once the delivery system handle is retained in the support device, the clinician may lock the delivery system in place with one or more fasteners to prevent rotational or linear translation of the delivery system. The clinician may then adjust the position of the distal end portion of the first and/or second catheter using the knobs or other translation mechanisms on the support device. By utilizing the support device, the clinician may have both hands free to adjust the position of the distal end of the delivery system on one or more planes. For example, the clinical may turn a knob connected to a first transition assembly of the support device to move the distal end portion along a first plane to a desired position. If the support device includes a second transition assembly, then the clinician may also turn a second knob to move the distal end portion along a second plane. The support device will also stabilize the delivery system, enabling the clinician to make fine-tune adjustments of the distal end to ensure precise deployment of the medical device at the correct position.

As a non-limiting example, a clinician may wish to deliver a mitral valve device to the mitral valve of a patient using the present disclosure. In one such example, the clinician may deliver a first distal end portion of a first catheter shaft and a second distal end portion of a second catheter shaft into the heart. The second catheter shaft may extend through and be longitudinally slidable with respect to the first catheter shaft. The clinician may then place a delivery system handle into a support device of the present disclosure. For example, the clinician may place a first handle component coupled to a first proximal portion of the first catheter shaft on a first base assembly. The clinician may further place a second handle component coupled to a second proximal portion of the second catheter shaft on a second base assembly and a third handle component coupled to a third catheter on a third base assembly. Once the handle components are retained, the clinician may translate the second base assembly with respect to the first base assembly to longitudinally translate the second handle component with respect to the first handle component, thereby causing the second distal end portion of the second catheter shaft to move along a first plane. To do this, the clinician may, for example, manipulate a first knob operably coupled to a first translation assembly. Manipulating the first knob may move the distal end portion of the second catheter in a proximal or distal direction. The clinician may also translate the third base assembly with respect to the second base assembly to longitudinally translate the third handle component with respect to the second handle component (and the first handle component), thereby causing the distal end portion of the third catheter shaft to advance or retract relative to the second catheter. To do this, the clinician may, for example, manipulate a second knob operably coupled to a second translation assembly. Manipulating the second knob may move the distal end portion of the third catheter between the left atrium and the left ventricle.

The above detailed description of examples of the disclosure are not intended to be exhaustive or to limit the disclosure to the precise forms disclosed above. Although specific examples of, and examples for, the disclosure are described above for illustrative purposes, various equivalent modifications are possible within the scope of the disclosure as those skilled in the relevant art will recognize. For example, although steps are presented in a given order, alternative examples may perform steps in a different order. The various examples described herein may also be combined to provide further examples.

From the foregoing, it will be appreciated that specific examples of the disclosure have been described herein for purposes of illustration, but well-known structures and functions have not been shown or described in detail to avoid unnecessarily obscuring the description of the examples of the disclosure. Where the context permits, singular or plural terms may also include the plural or singular term, respectively.

Clause 1: A support device for releasably retaining a delivery system handle while delivering a medical device to a target site within a human body, the support device comprising: a first base carrying a first support configured to engage a first handle component of the delivery system handle; a second base carrying a second support configured to engage a second handle component of the delivery system handle, wherein at least a portion of the second base is on the first base, wherein the first and second supports extend away from the first and second bases, respectively; and a first translation assembly operably coupled to the first base and the second base, wherein the first translation assembly is configured to slidably translate the second base with respect to the first base, and wherein the first translation assembly is configured to longitudinally translate the second handle component with respect to and independent of the first handle component when the delivery system handle is supported by the support device.

Clause 2: The support device of claim 1, further comprising: a third base carrying a third support configured to engage a third handle component of the delivery system handle, wherein at least a portion of the second base is positioned between the first base and the third base, and wherein the third support extends in a direction away from the third base; and a second translation assembly operably coupled to the second base and the third base, wherein the second translation assembly is configured to slidably translate the third base with respect to the second base to longitudinally translate the third handle component with respect to and independent of the second handle component when the delivery system handle is supported by the support device.

Clause 3: The support device of clause 1 or 2, further comprising a spacer component configured to space apart a portion of the first base from a surface on which the support device is configured to rest.

Clause 4: The support device of clause 3, wherein the spacer component is configured to orient the first base and the second base at an angle with respect to the surface on which the support device is configured to rest.

Clause 5: The support device of any one of clauses 1 to 4, wherein: the first translation assembly comprises a first rack, a first pinion, and a first knob operably coupled to the first pinion, the first pinion being configured to rotate upon manipulation of the first knob such that the first rack translates longitudinally with respect to the first pinion to move the first and second bases relative to each other.

Clause 6: The support device of clause 5, wherein a surface of the first base or the second based comprises the rack.

Clause 7: The support device of clause 6, wherein the rack comprises a plurality of spaced apart protrusions or a plurality of spaced apart apertures.

Clause 8: The support device of any one of clauses 1 to 4, wherein the first translation assembly comprises a worm gear.

Clause 9: The support device of any one of clauses 1 to 8, wherein: the first support comprises a first fastener configured to releasably secure the first handle component to the first base.

Clause 10: The support device of clause 2, wherein the third support comprises a back-support configured to engage a cross-sectional end portion of the delivery system handle.

Clause 11: The support device of any one of clauses 1 to 10, further comprising a platform, wherein the first base is coupled to the platform, and wherein the platform comprises a first end portion and a second end portion.

Clause 12: The support device of clause 11, wherein: the platform defines a platform axis extending through the first and second end portions; the first base has a first terminus proximate to the first end portion of the platform and a second terminus spaced apart from the first end portion along the platform axis; the first base has a first axis extending through the first and second termini of the first base; and the spacer component is configured to space the second terminus of the first base from the platform such that the platform axis and the first axis form an acute angle.

Clause 13: The support device of clause 12, wherein the spacer component is adjustable, and wherein adjusting the spacer component changes the acute angle.

Clause 14: A system for delivering a device into a heart of a patient, the system comprising: the support device of any one of claims 1 to 13; and a catheter system comprising: a first catheter device having a first elongated catheter shaft and a first handle component; and a second catheter device having a second elongated catheter shaft, a second handle component, and a third handle component, the third handle component configured to translate longitudinally with respect to the second handle component, the second elongated catheter shaft having a steerable distal end portion, wherein the second elongated catheter shaft is configured to extend through the first handle component and the first elongated catheter shaft, and wherein the second catheter device is configured to longitudinally translate with respect to the first catheter device.

Clause 15: The system of clause 14, wherein: the delivery system is configured to implant a prosthetic mitral device into the heart of the patient; and the first translation assembly is configured to translate the steerable distal end portion of the second elongated catheter shaft with respect to a distal end portion of the first elongated catheter shaft when the steerable distal end portion is positioned at or near a mitral valve annulus.

Clause 16: The system of clause 14 or 15, wherein the system further comprises a third catheter device having a third elongated catheter shaft, wherein the second translation assembly is configured to translate a distal end portion of the third elongated catheter shaft between a left atrium and left ventricle of the heart.

Clause 17: The system of any one of clauses 14 to 16, wherein: the first handle component comprises one or more first flanges configured to mate with one or more first grooves on the first support; and the second handle component comprises one or more second flanges configured to mate with one or more second grooves on the second support.

Clause 18: The system of any one of clauses 14 to 17, further comprising a coupling device, wherein the coupling device is configured to engage the support device and engage a support structure to position the support device relative to the support structure.

Clause 19: The system of clause 18, wherein the coupling device and the support device define a third translational assembly configured to cause the support device to longitudinally translate relative to the coupling device.

Clause 20: A method for delivering a device into a heart of a patient, the method comprising: delivering a first distal end portion of a first catheter shaft and a second distal end portion of a second catheter shaft into the heart, wherein the second catheter shaft extends through and is longitudinally slidable with respect to the first catheter shaft; supporting a first handle component on a first base assembly, wherein the first handle component is coupled to a first proximal portion of the first catheter shaft; supporting a second handle component on a second base assembly, wherein the second handle component is coupled to a second proximal portion of the second catheter shaft; supporting a third handle component on a third base assembly; translating the second base assembly with respect to the first base assembly to longitudinally translate the second handle component with respect to the first handle component, wherein the longitudinal translation of the second handle component translates the second distal end portion of the second catheter shaft along a first plane; and translating the third base assembly with respect to the second base assembly to longitudinally translate the third handle component with respect to the first handle component and the second handle component, wherein the longitudinal translation of the third handle component translates a distal end portion of a third catheter shaft relative to the to the second distal end portion.

Clause 21: The method of clause 20, further comprising positioning the second distal end portion of the second catheter shaft at or near a mitral valve annulus.

Clause 22: The method of clause 20 or 21, wherein translating the second distal end portion of the second catheter along a first plane comprises translating the steerable distal end portion of the second elongated catheter shaft in a lateral or medial direction when the steerable distal end portion is positioned at or near a mitral valve annulus.

Clause 23: The method of any one of clauses 20 to 22, wherein translating the distal end portion of the third catheter shaft comprises translating the distal end portion of the third elongated catheter shaft between a left atrium and left ventricle of the heart.

Clause 24: The method of any one of clauses 20 to 23, further comprising deploying the device at or near the mitral valve annulus.

As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific examples have been described herein for purposes of illustration, but that various modifications may be made without deviating from the disclosure. Further, while advantages associated with some examples of the disclosure have been described in the context of those examples, other examples may also exhibit such advantages, and not all examples need necessarily exhibit such advantages to fall within the scope of the disclosure. Accordingly, the disclosure and associated disclosure can encompass other examples not expressly shown or described herein. The following examples provide further representative examples of the present disclosure.

What is claimed is:

1. A support device for releasably retaining a delivery system handle while delivering a medical device to a target site within a human body, the support device comprising:
   a first base carrying a first support configured to engage a first handle component of the delivery system handle;
   a second base carrying a second support configured to engage a second handle component of the delivery system handle, wherein at least a portion of the second base is on the first base, wherein the first and second supports extend away from the first and second bases, respectively; and
   a first translation assembly operably coupled to the first base and the second base, wherein the first translation assembly is configured to slidably translate the second base with respect to the first base, and wherein the first translation assembly is configured to longitudinally translate the second handle component with respect to and independent of the first handle component when the delivery system handle is supported by the support device.

2. A support device for releasably retaining a delivery system handle while delivering a medical device to a target site within a human body, the support device comprising:
   a first base carrying a first support configured to engage a first handle component of the delivery system handle;
   a second base carrying a second support configured to engage a second handle component of the delivery system handle, wherein at least a portion of the second base is on the first base, wherein the first and second supports extend away from the first and second bases, respectively;
   a first translation assembly operably coupled to the first base and the second base, wherein the first translation assembly is configured to slidably translate the second base with respect to the first base, and wherein the first translation assembly is configured to longitudinally translate the second handle component with respect to and independent of the first handle component when the delivery system handle is supported by the support device;
   a third base carrying a third support configured to engage a third handle component of the delivery system handle, wherein at least a portion of the second base is positioned between the first base and the third base, and wherein the third support extends in a direction away from the third base; and
   a second translation assembly operably coupled to the second base and the third base, wherein the second translation assembly is configured to slidably translate the third base with respect to the second base to longitudinally translate the third handle component with respect to and independent of the second handle component when the delivery system handle is supported by the support device.

3. A support device for releasably retaining a delivery system handle while delivering a medical device to a target site within a human body, the support device comprising:
   a first base carrying a first support configured to engage a first handle component of the delivery system handle;
   a second base carrying a second support configured to engage a second handle component of the delivery system handle, wherein at least a portion of the second base is on the first base, wherein the first and second supports extend away from the first and second bases, respectively;
   a first translation assembly operably coupled to the first base and the second base, wherein the first translation assembly is configured to slidably translate the second base with respect to the first base, and wherein the first translation assembly is configured to longitudinally translate the second handle component with respect to and independent of the first handle component when the delivery system handle is supported by the support device; and
   a spacer component configured to space apart a portion of the first base from a surface on which the support device is configured to rest, wherein the spacer component is configured to orient the first base and the second base at an acute angle with respect to the surface on which the support device is configured to rest.

4. A support device for releasably retaining a delivery system handle while delivering a medical device to a target site within a human body, the support device comprising:
   a first base carrying a first support configured to engage a first handle component of the delivery system handle;
   a second base carrying a second support configured to engage a second handle component of the delivery system handle, wherein at least a portion of the second base is on the first base, wherein the first and second supports extend away from the first and second bases, respectively; and a first translation assembly operably coupled to the first base and the second base, wherein the first translation assembly is configured to slidably translate the second base with respect to the first base, and wherein the first translation assembly is configured to longitudinally translate the second handle component with respect to and independent of the first handle component when the delivery system handle is supported by the support device;

wherein the first translation assembly comprises a first rack, a first pinion, and a first knob operably coupled to the first pinion, the first pinion being configured to rotate upon manipulation of the first knob such that the first rack translates longitudinally with respect to the first pinion to move the first and second bases relative to each other.

5. The support device of claim 4, wherein a surface of the first base or the second base comprises the rack.

6. The support device of claim 5, wherein the rack comprises a plurality of spaced apart protrusions or a plurality of spaced apart apertures.

7. The support device of claim 1, wherein the first translation assembly comprises a worm gear.

8. The support device of claim 1, wherein:
the first support comprises a first fastener configured to releasably secure the first handle component to the first base.

9. The support device of claim 2, wherein the third support comprises a back-support configured to engage a cross-sectional end portion of the delivery system handle.

10. The support device of claim 3, further comprising a platform, wherein the first base is coupled to the platform, and wherein the platform comprises a first end portion and a second end portion.

11. The support device of claim 10, wherein:
the platform defines a platform axis extending through the first and second end portions;
the first base has a first terminus proximate to the first end portion of the platform and a second terminus spaced apart from the first end portion along the platform axis;
the first base has a first axis extending through the first and second termini of the first base; and
the spacer component is configured to space the second terminus of the first base from the platform such that the platform axis and the first axis form the acute angle.

12. The support device of claim 11, wherein the spacer component is adjustable, and wherein adjusting the spacer component changes the acute angle.

13. The support device of claim 2, further comprising a spacer component configured to space apart a portion of the first base from a surface on which the support device is configured to rest, wherein the spacer component is configured to orient the first base and the second base at an acute angle with respect to the surface on which the support device is configured to rest.

14. The support device of claim 2, wherein the first translation assembly comprises a first rack, a first pinion, and a first knob operably coupled to the first pinion, the first pinion being configured to rotate upon manipulation of the first knob such that the first rack translates longitudinally with respect to the first pinion to move the first and second bases relative to each other.

15. The support device of claim 14, wherein a surface of the first base or the second base comprises the rack.

16. The support device of claim 15, wherein the rack comprises a plurality of spaced apart protrusions or a plurality of spaced apart apertures.

17. The support device of claim 3, further comprising:
a third base carrying a third support configured to engage a third handle component of the delivery system handle, wherein at least a portion of the second base is positioned between the first base and the third base, and wherein the third support extends in a direction away from the third base; and
a second translation assembly operably coupled to the second base and the third base, wherein the second translation assembly is configured to slidably translate the third base with respect to the second base to longitudinally translate the third handle component with respect to and independent of the second handle component when the delivery system handle is supported by the support device.

18. The support device of claim 3, wherein the first translation assembly comprises a first rack, a first pinion, and a first knob operably coupled to the first pinion, the first pinion being configured to rotate upon manipulation of the first knob such that the first rack translates longitudinally with respect to the first pinion to move the first and second bases relative to each other.

19. The support device of claim 18, wherein a surface of the first base or the second base comprises the rack.

20. The support device of claim 18, wherein the rack comprises a plurality of spaced apart protrusions or a plurality of spaced apart apertures.

21. The support device of claim 4, further comprising a spacer component configured to space apart a portion of the first base from a surface on which the support device is configured to rest, wherein the spacer component is configured to orient the first base and the second base at an acute angle with respect to the surface on which the support device is configured to rest.

22. The support device of claim 4, further comprising:
a third base carrying a third support configured to engage a third handle component of the delivery system handle, wherein at least a portion of the second base is positioned between the first base and the third base, and wherein the third support extends in a direction away from the third base; and
a second translation assembly operably coupled to the second base and the third base, wherein the second translation assembly is configured to slidably translate the third base with respect to the second base to longitudinally translate the third handle component with respect to and independent of the second handle component when the delivery system handle is supported by the support device.

\* \* \* \* \*